(12) United States Patent
Desimone et al.

(10) Patent No.: US 12,239,365 B2
(45) Date of Patent: Mar. 4, 2025

(54) ELECTROPORATION FOR OBESITY OR DIABETES TREATMENT

(71) Applicant: Mayo Foundation for Medical Education and Research, Rochester, MN (US)

(72) Inventors: Christopher V. Desimone, Rochester, MN (US); Barham K. Abu Dayyeh, Rochester, MN (US); Samuel J. Asirvatham, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 17/529,037

(22) Filed: Nov. 17, 2021

(65) Prior Publication Data

US 2022/0071700 A1    Mar. 10, 2022

Related U.S. Application Data

(63) Continuation of application No. 15/766,604, filed as application No. PCT/US2016/055966 on Oct. 7, 2016, now Pat. No. 11,337,749.

(Continued)

(51) Int. Cl.
*A61B 18/14*     (2006.01)
*A61B 1/00*      (2006.01)
(Continued)

(52) U.S. Cl.
CPC ...... *A61B 18/1492* (2013.01); *A61B 1/00082* (2013.01); *A61B 1/00151* (2013.01);
(Continued)

(58) Field of Classification Search
CPC ...... A61B 18/1492; A61B 2018/00065; A61B 2018/00083; A61B 2018/0022;
(Continued)

(56) References Cited

U.S. PATENT DOCUMENTS

| 1,953,819 A | 4/1934 | Payne |
|---|---|---|
| 3,245,408 A | 4/1966 | Gonser |

(Continued)

FOREIGN PATENT DOCUMENTS

| AU | 2014200616 A1 | 2/2014 |
|---|---|---|
| CN | 103517731 A | 1/2014 |

(Continued)

OTHER PUBLICATIONS

American Diabetes Association, Standards of Medical Care in Diabetes-2020 Abridged for Primary Care Providers, Clinical diabetes: a publication of the American Diabetes Association, 2020, pp. 10-38, vol. 38, No. 1.

(Continued)

*Primary Examiner* — Michael F Peffley
*Assistant Examiner* — Amanda L Zink
(74) *Attorney, Agent, or Firm* — COOLEY LLP

(57) ABSTRACT

Endolumenal devices and methods can be used for the treatment of health conditions including obesity and diabetes. In some embodiments, the methods and systems provided herein can cause weight loss or control diabetes by reducing the caloric absorption of an individual. For example, this document provides several devices and methods for treating obesity and diabetes by using electroporation to modulate the duodenal mucosa. In addition, this document provides devices and methods for bypassing portions of the gastrointestinal tract to reduce nutritional uptake.

25 Claims, 8 Drawing Sheets

Related U.S. Application Data

(60) Provisional application No. 62/238,191, filed on Oct. 7, 2015.

(51) Int. Cl.
*A61B 90/00* (2016.01)
*A61N 1/32* (2006.01)
*A61N 1/36* (2006.01)
*A61B 18/00* (2006.01)
*A61B 18/12* (2006.01)
*A61M 25/10* (2013.01)

(52) U.S. Cl.
CPC ............ *A61B 90/361* (2016.02); *A61N 1/327* (2013.01); *A61N 1/36007* (2013.01); *A61B 2018/00065* (2013.01); *A61B 2018/00083* (2013.01); *A61B 2018/0016* (2013.01); *A61B 2018/0022* (2013.01); *A61B 2018/00238* (2013.01); *A61B 2018/00261* (2013.01); *A61B 2018/00285* (2013.01); *A61B 2018/00494* (2013.01); *A61B 2018/00577* (2013.01); *A61B 2018/00613* (2013.01); *A61B 2018/00839* (2013.01); *A61B 2018/00982* (2013.01); *A61B 2018/126* (2013.01); *A61B 2018/1467* (2013.01); *A61B 2018/1472* (2013.01); *A61B 2090/3966* (2016.02); *A61B 2218/002* (2013.01); *A61M 2025/1004* (2013.01); *A61M 25/1011* (2013.01); *A61M 2025/1015* (2013.01); *A61M 2025/10181* (2013.11); *A61M 2025/105* (2013.01); *A61M 2025/1052* (2013.01); *A61M 2025/1079* (2013.01)

(58) Field of Classification Search
CPC ........... A61B 2018/00238; A61B 2018/00261; A61B 2018/00285; A61B 2018/00494; A61B 2018/00577; A61B 2018/00613; A61B 2018/00839; A61B 2018/00982; A61B 2018/126; A61B 2018/1467; A61B 2018/1472; A61B 2090/3966; A61B 2218/002; A61B 90/361; A61B 1/00082; A61B 1/00151; A61B 2018/0016; A61M 2025/1004; A61M 2025/1015; A61M 2025/105; A61M 2025/1052; A61M 2025/1079; A61M 25/1011; A61M 25/10181; A61N 1/0412; A61N 1/0509; A61N 1/327; A61N 1/36007

See application file for complete search history.

(56) References Cited

U.S. PATENT DOCUMENTS

| | | |
|---|---|---|
| 4,325,374 A * | 4/1982 | Komiya ................. A61B 18/14 606/47 |
| 4,676,228 A | 6/1987 | Krasner et al. |
| 4,969,885 A | 11/1990 | Farin |
| 4,979,948 A * | 12/1990 | Geddes .............. A61B 18/1492 607/101 |
| 5,019,034 A | 5/1991 | Weaver et al. |
| 5,084,044 A | 1/1992 | Quint |
| 5,117,828 A | 6/1992 | Metzger et al. |
| 5,122,137 A | 6/1992 | Lennox |
| 5,137,817 A | 8/1992 | Busta et al. |
| 5,190,540 A | 3/1993 | Lee |
| 5,282,785 A | 2/1994 | Shapland et al. |
| 5,286,254 A | 2/1994 | Shapland et al. |
| 5,383,917 A | 1/1995 | Desai et al. |
| 5,419,763 A | 5/1995 | Hildebrand |
| 5,427,118 A | 6/1995 | Nita et al. |
| 5,464,386 A | 11/1995 | Hofmann |
| 5,498,238 A | 3/1996 | Shapland et al. |
| 5,505,700 A | 4/1996 | Leone et al. |
| 5,507,724 A | 4/1996 | Hofmann et al. |
| 5,515,100 A | 5/1996 | Nogo |
| 5,549,603 A | 8/1996 | Feiring |
| 5,575,772 A | 11/1996 | Lennox |
| 5,674,267 A | 10/1997 | Mir et al. |
| 5,697,281 A | 12/1997 | Eggers et al. |
| 5,702,359 A | 12/1997 | Hofmann et al. |
| 5,704,908 A | 1/1998 | Hofmann et al. |
| 5,800,484 A | 9/1998 | Gough et al. |
| 5,807,306 A | 9/1998 | Shapland et al. |
| 5,810,762 A | 9/1998 | Hofmann |
| 5,879,349 A | 3/1999 | Edwards |
| 5,944,710 A | 8/1999 | Dev et al. |
| 5,964,753 A | 10/1999 | Edwards |
| 5,968,012 A | 10/1999 | Ren et al. |
| 6,027,488 A | 2/2000 | Hofmann et al. |
| 6,045,532 A | 4/2000 | Eggers et al. |
| 6,053,937 A | 4/2000 | Edwards et al. |
| 6,055,453 A | 4/2000 | Hofmann et al. |
| 6,056,744 A | 5/2000 | Edwards |
| 6,068,650 A | 5/2000 | Hofmann et al. |
| 6,086,581 A | 7/2000 | Reynolds et al. |
| 6,112,123 A | 8/2000 | Kelleher et al. |
| 6,120,493 A | 9/2000 | Hofmann |
| 6,162,237 A | 12/2000 | Chan |
| 6,216,034 B1 | 4/2001 | Hofmann et al. |
| 6,219,577 B1 | 4/2001 | Brown, II et al. |
| 6,233,482 B1 | 5/2001 | Hofmann et al. |
| 6,241,701 B1 | 6/2001 | Hofmann |
| 6,325,777 B1 | 12/2001 | Zadno-Azizi et al. |
| 6,326,177 B1 | 12/2001 | Schoenbach et al. |
| 6,389,314 B2 | 5/2002 | Feiring |
| 6,428,538 B1 | 8/2002 | Blewett et al. |
| 6,516,223 B2 | 2/2003 | Hofmann |
| 6,529,778 B2 | 3/2003 | Prutchi |
| 6,542,778 B1 | 4/2003 | Fuhr et al. |
| 6,582,423 B1 | 6/2003 | Thapliyal et al. |
| 6,675,809 B2 | 1/2004 | Stack et al. |
| 6,678,558 B1 | 1/2004 | Dimmer et al. |
| 6,697,669 B2 | 2/2004 | Dev et al. |
| 6,697,670 B2 | 2/2004 | Chomenky et al. |
| 6,714,861 B2 | 3/2004 | Okude et al. |
| 6,758,846 B2 | 7/2004 | Goble et al. |
| 6,795,728 B2 | 9/2004 | Chornenky et al. |
| 6,905,496 B1 | 6/2005 | Ellman et al. |
| 6,936,024 B1 | 8/2005 | Houser |
| 6,978,172 B2 | 12/2005 | Mori et al. |
| 6,994,706 B2 | 2/2006 | Chornenky et al. |
| 7,004,941 B2 | 2/2006 | Tvinnereim et al. |
| 7,054,685 B2 | 5/2006 | Dimmer et al. |
| 7,150,745 B2 | 12/2006 | Stern et al. |
| 7,175,669 B2 | 2/2007 | Geitz |
| 7,220,284 B2 | 5/2007 | Kagan et al. |
| 7,272,050 B2 | 9/2007 | Han et al. |
| 7,285,117 B2 | 10/2007 | Krueger et al. |
| 7,326,207 B2 * | 2/2008 | Edwards ............... A61F 5/0026 606/41 |
| 7,412,284 B2 | 8/2008 | Hofmann |
| 7,422,587 B2 | 9/2008 | Bek et al. |
| 7,458,378 B2 | 12/2008 | Utley et al. |
| 7,571,729 B2 | 8/2009 | Saadat et al. |
| 7,620,451 B2 | 11/2009 | Demarais et al. |
| 7,737,109 B2 | 6/2010 | Miller |
| 7,742,795 B2 | 6/2010 | Stone et al. |
| 7,758,623 B2 | 7/2010 | Dzeng et al. |
| 7,904,172 B2 | 3/2011 | Kon et al. |
| 7,909,755 B2 | 3/2011 | Itoi |
| 7,959,627 B2 | 6/2011 | Utley et al. |
| 8,032,207 B2 | 10/2011 | Lapanashvili et al. |
| 8,048,067 B2 | 11/2011 | Davalos et al. |
| 8,221,411 B2 | 7/2012 | Francischelli et al. |
| 8,251,986 B2 | 8/2012 | Chornenky et al. |
| 8,267,932 B2 | 9/2012 | Baxter et al. |
| 8,282,631 B2 | 10/2012 | Davalos et al. |
| 8,323,229 B2 | 12/2012 | Shin et al. |
| 8,355,799 B2 | 1/2013 | Marion et al. |
| 8,361,066 B2 | 1/2013 | Long et al. |

(56) References Cited

U.S. PATENT DOCUMENTS

| | | |
|---|---|---|
| 8,428,735 B2 | 4/2013 | Littlewood et al. |
| 8,473,051 B1 | 6/2013 | Wessels et al. |
| 8,529,612 B2 | 9/2013 | Singh |
| 8,562,588 B2 | 10/2013 | Hobbs et al. |
| 8,636,648 B2 | 1/2014 | Gazdzinski |
| 8,647,338 B2 | 2/2014 | Chornenky et al. |
| 8,740,894 B2 | 6/2014 | Edwards |
| 8,790,339 B2 | 7/2014 | Edwards et al. |
| 8,814,860 B2 | 8/2014 | Davalos et al. |
| 8,915,911 B2 | 12/2014 | Azure |
| 8,926,576 B2 | 1/2015 | Mikkaichi |
| 8,926,606 B2 | 1/2015 | Davalos et al. |
| 9,005,100 B2 | 4/2015 | Gnanashanmugam et al. |
| 9,005,189 B2 | 4/2015 | Davalos et al. |
| 9,011,431 B2 | 4/2015 | Long et al. |
| 9,078,665 B2 | 7/2015 | Moss et al. |
| 9,119,600 B2 | 9/2015 | Richardson et al. |
| 9,168,096 B2 | 10/2015 | Kreindel |
| 9,173,704 B2 | 11/2015 | Hobbs et al. |
| 9,179,970 B2 | 11/2015 | Utley et al. |
| 9,191,801 B2 | 11/2015 | Kwak |
| 9,198,733 B2 | 12/2015 | Neal, II et al. |
| 9,277,957 B2 | 3/2016 | Long et al. |
| 9,283,051 B2 | 3/2016 | Garcia et al. |
| 9,289,606 B2 | 3/2016 | Paul et al. |
| 9,308,043 B2 | 4/2016 | Zarins et al. |
| 9,314,620 B2 | 4/2016 | Long et al. |
| 9,345,538 B2 | 5/2016 | Deem et al. |
| 9,351,789 B2 | 5/2016 | Novichenok et al. |
| 9,351,790 B2 | 5/2016 | Zemel et al. |
| 9,358,020 B2 | 6/2016 | Smith |
| 9,462,960 B2 | 10/2016 | Kassab |
| 9,480,524 B2 | 11/2016 | Chorenky et al. |
| 9,555,020 B2 | 1/2017 | Pasricha et al. |
| 9,597,147 B2 | 3/2017 | Jackson et al. |
| 9,598,691 B2 | 3/2017 | Davalos |
| 9,737,360 B2 | 8/2017 | West et al. |
| 9,788,885 B2 | 10/2017 | Long et al. |
| 9,801,681 B2 | 10/2017 | Laske et al. |
| 9,827,041 B2 | 11/2017 | Zarins et al. |
| 9,861,435 B2 | 1/2018 | Richardson et al. |
| 9,867,652 B2 | 1/2018 | Sano et al. |
| 9,918,789 B2 | 3/2018 | Bagley et al. |
| 9,924,991 B2 | 3/2018 | West et al. |
| 9,937,344 B2 | 4/2018 | Starkebaum et al. |
| 9,988,885 B1 | 6/2018 | Shahinpour et al. |
| 9,993,297 B2 | 6/2018 | Ben-Oren et al. |
| 9,999,467 B2 | 6/2018 | Moss et al. |
| 10,004,558 B2 | 6/2018 | Long et al. |
| 10,010,666 B2 | 7/2018 | Rubinsky et al. |
| 10,016,232 B1 | 7/2018 | Bowers et al. |
| 10,039,596 B2 | 8/2018 | Zarins et al. |
| 10,064,697 B2 | 9/2018 | Sharma et al. |
| 10,070,914 B2 | 9/2018 | Schoenbach et al. |
| 10,117,701 B2 | 11/2018 | Davalos et al. |
| 10,154,874 B2 | 12/2018 | Davalos et al. |
| 10,154,876 B2 | 12/2018 | Callas et al. |
| 10,238,447 B2 | 3/2019 | Neal, II et al. |
| 10,245,098 B2 | 4/2019 | Davalos et al. |
| 10,245,105 B2 | 4/2019 | Davalos |
| 10,292,755 B2 | 5/2019 | Arena et al. |
| 10,299,857 B2 | 5/2019 | Rajagopalan et al. |
| 10,322,286 B2 | 6/2019 | Viswanathan et al. |
| 10,342,598 B2 | 7/2019 | Long et al. |
| 10,349,998 B2 | 7/2019 | Levin et al. |
| 10,350,004 B2 | 7/2019 | Gifford, III et al. |
| 10,368,944 B2 | 8/2019 | Schaer |
| 10,448,989 B2 | 10/2019 | Arena et al. |
| 10,463,426 B2 | 11/2019 | Chornenky et al. |
| 10,548,653 B2 | 2/2020 | Hoey et al. |
| 10,558,665 B2 | 2/2020 | Mazumder |
| 10,569,081 B2 | 2/2020 | Howard |
| 10,582,963 B2 | 3/2020 | Woloszko et al. |
| 10,610,663 B2 | 4/2020 | Rajagopalan et al. |
| 10,614,949 B2 | 4/2020 | Smith et al. |
| 10,722,302 B2 | 7/2020 | Sherman et al. |
| 10,722,305 B2 | 7/2020 | Moss et al. |
| 10,765,474 B2 | 9/2020 | Kadamus et al. |
| 10,842,668 B2 | 11/2020 | Singh |
| 10,856,926 B2 | 12/2020 | Azamian et al. |
| 10,869,718 B2 | 12/2020 | Rajagopalan et al. |
| 10,881,455 B2 | 1/2021 | Schwartz et al. |
| 10,888,377 B2 | 1/2021 | Ben-Oren et al. |
| 10,898,263 B2 | 1/2021 | Bagley et al. |
| 10,912,609 B2 | 2/2021 | De La Rama et al. |
| 10,939,949 B2 | 3/2021 | Rubinsky et al. |
| 10,946,193 B2 | 3/2021 | Athos et al. |
| 10,953,241 B2 | 3/2021 | Luttrull et al. |
| 10,959,774 B2 | 3/2021 | Kadamus et al. |
| 10,973,561 B2 | 4/2021 | Caplan et al. |
| 10,987,149 B2 | 4/2021 | Rajagopalan et al. |
| 11,103,674 B2 | 8/2021 | Rajagopalan et al. |
| 11,185,367 B2 | 11/2021 | Rajagopalan et al. |
| 11,246,639 B2 | 2/2022 | Rajagopalan et al. |
| 11,254,926 B2 | 2/2022 | Neal, II et al. |
| 11,272,979 B2 | 3/2022 | Garcia et al. |
| 11,278,349 B2 | 3/2022 | Stewart et al. |
| 11,298,175 B2 | 4/2022 | Konings |
| 11,311,333 B2 | 4/2022 | Rajagopalan et al. |
| 11,337,749 B2 | 5/2022 | Desimone et al. |
| 11,357,978 B2 | 6/2022 | Bowers et al. |
| 11,364,072 B2 | 6/2022 | Howard et al. |
| 11,376,064 B2 | 7/2022 | Rankin |
| 11,382,681 B2 | 7/2022 | Arena et al. |
| 11,389,171 B2 | 7/2022 | Goldsmith |
| 11,419,659 B2 | 8/2022 | Levin et al. |
| 11,439,457 B2 | 9/2022 | Caplan et al. |
| 11,453,873 B2 | 9/2022 | Davalos et al. |
| 11,464,968 B2 | 10/2022 | Howard |
| 11,471,208 B2 | 10/2022 | Waldstreicher et al. |
| 11,547,851 B2 | 1/2023 | Krimsky et al. |
| 11,596,474 B2 | 3/2023 | Van Der Weide et al. |
| 11,638,603 B2 | 5/2023 | Sano et al. |
| 11,638,819 B2 | 5/2023 | Gundert et al. |
| 11,655,466 B2 | 5/2023 | Neal, II et al. |
| 11,723,712 B2 | 8/2023 | Athos et al. |
| 11,826,521 B2 | 11/2023 | Rajagopalan et al. |
| 11,878,128 B2 | 1/2024 | Rajagopalan et al. |
| 11,912,975 B2 | 2/2024 | Soden et al. |
| 2001/0044596 A1 | 11/2001 | Jaafar |
| 2002/0087208 A1 | 7/2002 | Koblish et al. |
| 2003/0055464 A1* | 3/2003 | Darvish .............. A61N 1/05 607/40 |
| 2003/0093072 A1 | 5/2003 | Friedman |
| 2003/0153905 A1 | 8/2003 | Edwards et al. |
| 2003/0181898 A1 | 9/2003 | Bowers |
| 2003/0236496 A1 | 12/2003 | Samson et al. |
| 2004/0095100 A1 | 5/2004 | Thompson |
| 2004/0215180 A1 | 10/2004 | Starkebaum et al. |
| 2004/0215296 A1 | 10/2004 | Ganz et al. |
| 2004/0220559 A1 | 11/2004 | Kramer et al. |
| 2004/0236376 A1 | 11/2004 | Miklavcic et al. |
| 2005/0090873 A1* | 4/2005 | Imran .............. A61N 1/36007 607/40 |
| 2005/0183732 A1* | 8/2005 | Edwards ............. A61F 5/0026 606/41 |
| 2005/0192652 A1 | 9/2005 | Cioanta et al. |
| 2005/0234293 A1 | 10/2005 | Yamamoto et al. |
| 2006/0084962 A1 | 4/2006 | Joye et al. |
| 2006/0095032 A1 | 5/2006 | Jackson et al. |
| 2006/0135963 A1 | 6/2006 | Kick et al. |
| 2006/0217698 A1 | 9/2006 | Starkebaum et al. |
| 2006/0293730 A1 | 12/2006 | Rubinsky et al. |
| 2007/0016262 A1* | 1/2007 | Gross ................ A61N 1/36007 607/40 |
| 2007/0043345 A1 | 2/2007 | Davalos et al. |
| 2007/0100355 A1 | 5/2007 | Bonde et al. |
| 2007/0225800 A1 | 9/2007 | Sahatjian |
| 2008/0058786 A1 | 3/2008 | Boyden et al. |
| 2008/0058887 A1* | 3/2008 | Griffin .............. A61N 1/36007 607/40 |
| 2008/0207994 A1 | 8/2008 | Gonon |
| 2008/0223380 A1 | 9/2008 | Chinn |

(56) References Cited

U.S. PATENT DOCUMENTS

| | | | |
|---|---|---|---|
| 2008/0275445 A1* | 11/2008 | Kelly | A61B 18/1492 606/45 |
| 2009/0012469 A1 | 1/2009 | Nita | |
| 2009/0203995 A1 | 8/2009 | Matonick | |
| 2009/0248012 A1 | 10/2009 | Maor et al. | |
| 2009/0269317 A1 | 10/2009 | Davalos | |
| 2009/0281477 A1* | 11/2009 | Mikus | A61B 18/1477 606/41 |
| 2010/0023004 A1 | 1/2010 | Francischelli et al. | |
| 2010/0023047 A1 | 1/2010 | Simpson | |
| 2010/0114325 A1 | 5/2010 | Yang et al. | |
| 2010/0179530 A1 | 7/2010 | Long et al. | |
| 2010/0191235 A1 | 7/2010 | Moshe et al. | |
| 2010/0204560 A1 | 8/2010 | Salahieh et al. | |
| 2010/0210994 A1 | 8/2010 | Zarif | |
| 2010/0222677 A1 | 9/2010 | Placek et al. | |
| 2010/0249771 A1 | 9/2010 | Pearson et al. | |
| 2010/0256630 A1 | 10/2010 | Hamilton et al. | |
| 2011/0091564 A1 | 4/2011 | Chu | |
| 2011/0106273 A1 | 5/2011 | Belhe et al. | |
| 2011/0118732 A1 | 5/2011 | Rubinsky et al. | |
| 2011/0144635 A1 | 6/2011 | Harper et al. | |
| 2011/0160514 A1 | 6/2011 | Long et al. | |
| 2011/0172659 A1 | 7/2011 | Brannan | |
| 2011/0208175 A1 | 8/2011 | Sobotka et al. | |
| 2011/0224768 A1 | 9/2011 | Edwards | |
| 2011/0288543 A1 | 11/2011 | Cheng et al. | |
| 2012/0010610 A1 | 1/2012 | Keppel | |
| 2012/0041465 A1 | 2/2012 | Shalon | |
| 2012/0059255 A1 | 3/2012 | Paul et al. | |
| 2012/0109122 A1 | 5/2012 | Arena et al. | |
| 2012/0116266 A1 | 5/2012 | Houser et al. | |
| 2012/0191089 A1 | 7/2012 | Gonzalez et al. | |
| 2012/0259269 A1 | 10/2012 | Meyer | |
| 2013/0030430 A1 | 1/2013 | Stewart et al. | |
| 2013/0178910 A1* | 7/2013 | Azamian | A61K 9/0019 607/33 |
| 2013/0184702 A1 | 7/2013 | Neal, II et al. | |
| 2013/0190675 A1 | 7/2013 | Sandoski | |
| 2013/0345670 A1 | 12/2013 | Rajagopalan et al. | |
| 2014/0031810 A1 | 1/2014 | Mahvi et al. | |
| 2014/0074077 A1 | 3/2014 | Lane | |
| 2014/0088362 A1 | 3/2014 | Terliuc et al. | |
| 2014/0088529 A1 | 3/2014 | Bengtson | |
| 2014/0114304 A1 | 4/2014 | Wang et al. | |
| 2014/0121646 A1 | 5/2014 | Lodin et al. | |
| 2014/0135606 A1 | 5/2014 | Yasui | |
| 2014/0214026 A1 | 7/2014 | Degen | |
| 2014/0371736 A1 | 12/2014 | Levin et al. | |
| 2015/0141987 A1 | 5/2015 | Caplan et al. | |
| 2015/0148738 A1 | 5/2015 | Caplan et al. | |
| 2015/0164584 A1 | 6/2015 | Davalos et al. | |
| 2015/0173824 A1 | 6/2015 | Davalos et al. | |
| 2015/0182282 A1* | 7/2015 | Zemel | A61B 18/1206 606/41 |
| 2015/0182735 A1 | 7/2015 | Chang et al. | |
| 2015/0216592 A1 | 8/2015 | Gnanashanmugam et al. | |
| 2015/0289923 A1 | 10/2015 | Davalos et al. | |
| 2015/0327944 A1 | 11/2015 | Neal, II et al. | |
| 2016/0051324 A1 | 2/2016 | Stewart et al. | |
| 2016/0058493 A1 | 3/2016 | Neal, II et al. | |
| 2016/0066977 A1 | 3/2016 | Neal, II et al. | |
| 2016/0081745 A1 | 3/2016 | Rajagopalan et al. | |
| 2016/0175582 A1 | 6/2016 | Serna et al. | |
| 2016/0235470 A1 | 8/2016 | Callas et al. | |
| 2016/0287314 A1 | 10/2016 | Arena et al. | |
| 2016/0331441 A1 | 11/2016 | Konings | |
| 2016/0338761 A1 | 11/2016 | Chornenky et al. | |
| 2016/0354142 A1 | 12/2016 | Pearson et al. | |
| 2016/0361109 A1 | 12/2016 | Weaver et al. | |
| 2016/0367310 A1 | 12/2016 | Onik et al. | |
| 2016/0374754 A1 | 12/2016 | Asirvatham et al. | |
| 2017/0000559 A1 | 1/2017 | Rioux et al. | |
| 2017/0014183 A1 | 1/2017 | Gifford, III et al. | |
| 2017/0035501 A1 | 2/2017 | Chornenky et al. | |
| 2017/0095290 A1 | 4/2017 | Sherman et al. | |
| 2017/0105781 A1 | 4/2017 | Pasricha et al. | |
| 2017/0112562 A1 | 4/2017 | Woloszko et al. | |
| 2017/0203132 A1 | 7/2017 | Luttrull et al. | |
| 2017/0232269 A1 | 8/2017 | Luttrull et al. | |
| 2017/0245928 A1 | 8/2017 | Xiao et al. | |
| 2017/0265929 A1 | 9/2017 | Callas et al. | |
| 2017/0333122 A1 | 11/2017 | Rajagopalan et al. | |
| 2017/0348049 A1 | 12/2017 | Vrba et al. | |
| 2018/0021084 A1 | 1/2018 | Onik et al. | |
| 2018/0028252 A1 | 2/2018 | Lalonde | |
| 2018/0028264 A1 | 2/2018 | Onik et al. | |
| 2018/0042661 A1 | 2/2018 | Long et al. | |
| 2018/0043153 A1 | 2/2018 | Viswanathan et al. | |
| 2018/0071014 A1 | 3/2018 | Neal et al. | |
| 2018/0125575 A1 | 5/2018 | Schwartz et al. | |
| 2018/0193082 A1 | 7/2018 | Rubinsky et al. | |
| 2018/0193090 A1 | 7/2018 | de la Rama et al. | |
| 2018/0193590 A1 | 7/2018 | Rajagopalan et al. | |
| 2018/0214202 A1 | 8/2018 | Howard et al. | |
| 2018/0221622 A1 | 8/2018 | Rajagopalan et al. | |
| 2018/0250074 A1 | 9/2018 | Ben-Oren et al. | |
| 2018/0250508 A1 | 9/2018 | Howard | |
| 2018/0263694 A1 | 9/2018 | Moss et al. | |
| 2019/0069949 A1 | 3/2019 | Vrba et al. | |
| 2019/0175248 A1 | 6/2019 | Neal, II et al. | |
| 2019/0223938 A1 | 7/2019 | Arena et al. | |
| 2019/0223948 A1 | 7/2019 | Stewart et al. | |
| 2019/0233809 A1 | 8/2019 | Neal, II et al. | |
| 2019/0254740 A1 | 8/2019 | Koya et al. | |
| 2019/0256839 A1 | 8/2019 | Neal, II et al. | |
| 2019/0282294 A1 | 9/2019 | Davalos et al. | |
| 2019/0328445 A1 | 10/2019 | Sano et al. | |
| 2019/0344053 A1 | 11/2019 | Wang et al. | |
| 2019/0376055 A1 | 12/2019 | Davalos et al. | |
| 2020/0060758 A1 | 2/2020 | Rajagopalan et al. | |
| 2020/0060942 A1 | 2/2020 | Rajagopalan et al. | |
| 2020/0093541 A9 | 3/2020 | Neal, II et al. | |
| 2020/0129230 A1 | 4/2020 | Forsyth et al. | |
| 2020/0155217 A1 | 5/2020 | Morneau et al. | |
| 2020/0315700 A1 | 10/2020 | Petitpierre et al. | |
| 2020/0323576 A1 | 10/2020 | Neal et al. | |
| 2021/0113265 A1 | 4/2021 | D'agostino et al. | |
| 2021/0161582 A1 | 6/2021 | Byrd et al. | |
| 2021/0393327 A1 | 12/2021 | Eyster et al. | |
| 2022/0022952 A1 | 1/2022 | Koop et al. | |
| 2022/0054184 A9 | 2/2022 | Rajagopalan et al. | |
| 2022/0071700 A1 | 3/2022 | Desimone | |
| 2022/0117658 A1 | 4/2022 | Rajagopalan et al. | |
| 2022/0265337 A1 | 8/2022 | Rajagopalan et al. | |
| 2022/0331601 A1 | 10/2022 | D'Agostino et al. | |
| 2022/0354571 A1 | 11/2022 | Caplan et al. | |
| 2023/0000543 A1 | 1/2023 | Sano et al. | |
| 2023/0149706 A1 | 5/2023 | Krimsky et al. | |
| 2023/0165621 A1 | 6/2023 | Biasella et al. | |
| 2023/0172650 A1 | 6/2023 | Castellvi et al. | |
| 2023/0200883 A1 | 6/2023 | Caplan et al. | |
| 2023/0233250 A1 | 7/2023 | Rajagopalan et al. | |
| 2023/0310066 A1 | 10/2023 | Tegg et al. | |
| 2023/0380897 A1 | 11/2023 | Liu et al. | |
| 2023/0414274 A1 | 12/2023 | Moss et al. | |
| 2024/0016536 A1 | 1/2024 | Kato et al. | |
| 2024/0156523 A1 | 5/2024 | D'Agostino et al. | |
| 2024/0180613 A1 | 6/2024 | D'Agostino et al. | |

FOREIGN PATENT DOCUMENTS

| | | |
|---|---|---|
| EP | 2 865 349 A1 | 4/2015 |
| EP | 3 050 531 A1 | 8/2016 |
| EP | 3 316 813 A1 | 5/2018 |
| EP | 3 169 260 B1 | 9/2019 |
| JP | 2015097780 A | 5/2015 |
| JP | 2019516512 A | 6/2019 |
| WO | WO-1991/16945 A1 | 11/1991 |
| WO | WO-9519735 A1 | 7/1995 |
| WO | WO-1998/15318 A1 | 4/1998 |
| WO | WO-2000/35349 A1 | 6/2000 |
| WO | WO-2001068015 | 9/2001 |
| WO | WO-2005/089433 A2 | 9/2005 |

(56) References Cited

FOREIGN PATENT DOCUMENTS

| WO | WO-2005/089433 A3 | 9/2005 |
|---|---|---|
| WO | WO-2008137757 A1 | 11/2008 |
| WO | WO-2009009444 A1 | 1/2009 |
| WO | WO-2009132190 A2 | 10/2009 |
| WO | WO-2011/017387 A3 | 4/2011 |
| WO | WO-2011/047387 A2 | 4/2011 |
| WO | WO-2011/072221 A1 | 6/2011 |
| WO | WO-2012078522 A1 | 6/2012 |
| WO | WO-2012088149 A2 | 6/2012 |
| WO | WO-2012099974 A2 | 7/2012 |
| WO | WO-2012/161875 A1 | 11/2012 |
| WO | WO-2013012892 A2 | 1/2013 |
| WO | WO-2013116822 A1 | 8/2013 |
| WO | WO-2013130655 A1 | 9/2013 |
| WO | WO-2014/026055 A1 | 2/2014 |
| WO | WO-2014022436 A1 | 2/2014 |
| WO | WO-2014055997 A1 | 4/2014 |
| WO | WO-2014/118782 A2 | 8/2014 |
| WO | WO-2014/118782 A3 | 8/2014 |
| WO | WO-2014118738 A1 | 8/2014 |
| WO | WO-2014121664 A1 | 8/2014 |
| WO | WO-2014/189887 A2 | 11/2014 |
| WO | WO-2014/189887 A3 | 11/2014 |
| WO | WO-2014197632 A2 | 12/2014 |
| WO | WO-2015148541 A1 | 10/2015 |
| WO | WO-2015159296 A1 | 10/2015 |
| WO | WO-2016011269 A1 | 1/2016 |
| WO | WO-2016115031 A2 | 7/2016 |
| WO | WO-2016/178697 A1 | 11/2016 |
| WO | WO-2017/004432 A1 | 1/2017 |
| WO | WO-2017/062753 A1 | 4/2017 |
| WO | WO-2017/203380 A1 | 11/2017 |
| WO | WO-2017/212257 A1 | 12/2017 |
| WO | WO-2018/050025 A1 | 3/2018 |
| WO | WO-2018/089773 A1 | 5/2018 |
| WO | WO-2018/140473 A1 | 8/2018 |
| WO | WO-2018/167451 A1 | 9/2018 |
| WO | WO-2019018362 A1 | 1/2019 |
| WO | WO-2019136240 A1 | 7/2019 |
| WO | WO-2021081131 A1 | 4/2021 |
| WO | WO-2022171141 A1 | 8/2022 |
| WO | WO-2022226113 A1 | 10/2022 |
| WO | WO-2022260723 A1 | 12/2022 |
| WO | WO-2023280822 A1 | 1/2023 |
| WO | WO-2023086537 A1 | 5/2023 |
| WO | WO-2023093514 A1 | 6/2023 |
| WO | WO-2023147319 A1 | 8/2023 |
| WO | WO-2023150215 A1 | 8/2023 |
| WO | WO-2023161492 A1 | 8/2023 |
| WO | WO-2023172773 A1 | 9/2023 |
| WO | WO-2023122100 A3 | 11/2023 |

OTHER PUBLICATIONS

Arena et al., High-frequency irreversible electroporation (H-FIRE) for non-thermal ablation without muscle contraction, Biomedical Engineering OnLine, 2011, 21 pages, vol. 10, No. 102.
Cersosimo, et al., Pathogenesis of Type 2 Diabetes Mellitus, In Feingold KR, Anawalt B, Boyce A et al., ed. Endotext [Internet], 2020, 45 pages.
Dong, et al., First Human Trial of High-Frequency Irreversible Electroporation Therapy for Prostate Cancer, Technolology in Cancer Res. Treatment, 2018, pp. 1-9, vol. 17.
DPP Research Group, The Diabetes Prevention Program (DPP), Diabetes Care, 2002, pp. 2165-2171, vol. 25.
European Patent Office, Extended European Search Report for EP Application No. 16 854 413.8, Aug. 20, 2019, 12 pages.
European Patent Office, International Search Report and Writen Opinion for PCT/US2020/056720, Apr. 14, 2021, 20 pages.
Gilmer, et al., The cost to health plans of poor glycemic control, Diabetes Care, 1997, pp. 1847-1853, vol. 20.
Knavel, et al., Tumor Ablation: Common Modalities and General Practices, Tech. Vasc. Interv. Radiol., 2013, pp. 192-200, vol. 16.
Martin, Use of irreversible electroporation in unresectable pancreatic cancer, 2015, pp. 211-215, vol. 4.
Narayanan, Irreversible Electroporation, Semin Interv Radiol., 2015, pp. 349-355, vol. 32.
Ringel-Scaia, et al., High-frequency irreversible electroporation is an effective tumor ablation strategy that induces immunologic cell death and promotes systemic anti-tumor immunity, EbioMedicine, 2019, pp. 112-125, vol. 44.
Sami, et al., The Los Angeles Classification of Gastroesophageal Reflux Disease, Video J. Encycl. GI Endosc., 2012, pp. 103-104, vol. 1.
Samihah Zura Mohd Nani, What is the best solvent for drugs?, 2015, 3 pages.
Siddiqui, et al., High-Frequency Irreversible Electroporation: Safety and Efficacy of Next-Generation Irreversible Electroporation Adjacent to Critical Hepatic Structures, Surg. Innov., 2017, pp. 276-283, vol. 24.
Theodorakis, et al., Human duodenal enteroendocrine cells: source of both incretin peptides, GLP-1 and GIP, Am. J. Physiol. Endocrinol. Metab., 2006, E550-E559, vol. 290.
Van Baar, et al., Endoscopic duodenal mucosal resurfacing for the treatment of type 2 diabetes mellitus: one year results from the first international, open-label, prospective, multicentre study, Gut, 2019, pp. 295-303, vol. 69.
Verdam, et al., Small Intestinal Alterations in Severely Obese Hyperglycemic Subjects, J. Clin. Endocrinol. Metab., 2011, pp. E379-E383, vol. 96.
Wagner, et al., Effect of Improved Glycemic Control on Health Care Costs and Utilization, JAMA, 2001, pp. 182-189,. vol. 285.
United States Patent and Trademark Office, Non-Final Office Action for U.S. Appl. No. 15/766,604 Oct. 19, 2020, 15 pages.
United States Patent and Trademark Office, Final Office Action for U.S. Appl. No. 15/766,604 Feb. 19, 2021, 17 pages.
United States Patent and Trademark Office, Non-Final Office Action for U.S. Appl. No. 15/766,604 Jul. 2, 2021, 13 pages.
United States Patent and Trademark Office, Notice of Allowance for U.S. Appl. No. 15/766,604 Nov. 5, 2021, 8 pages.
United States Patent and Trademark Office, Notice of Allowance for U.S. Appl. No. 15/766,604 Feb. 25, 2022, 7 pages.
United States Patent and Trademark Office, International Search Report and Written Opinion for PCT/US2016/055966, Dec. 29, 2016, 14 pages.
International Search Report and Written Opinion for International Application No. PCT/US2022/025630 dated Aug. 8, 2022, 14 pages.
Non-Final Office Action for U.S. Appl. No. 17/076,692 dated May 26, 2023, 17 pages.
Final Office Action for U.S. Appl. No. 17/076,692, mailed Dec. 21, 2023, 21 pages.
International Search Report and Written Opinion in Intl. Application No. PCT/US2022/049653, mailed Mar. 27, 2023, 10 pages.
Adams et al., "Theoretical design and evaluation of endoluminal ultrasound applicators for thermal therapy of pancreatic cancer under image guidance," AIP Conference Proceedings, Mar. 17, 2017, vol. 1821, No. 1, 6 pages.
Al Sakere et al., "Tumor Ablation with Irreversible Electroporation," PLoS One, Nov. 7, 2007, No. 11, e1135, 8 pages.
Arena et al., "Advances in Therapeutic Electroporation to Mitigate Muscle Contractions," Journal of Membrane Science & Technology, 2012, vol. 2, No. 10.4172, pp. 2155-9589.
Arena et al., "Theoretical Considerations of Tissue Electroporation With High-Frequency Bipolar Pulses," IEEE Transactions on Biomedic, Dec. 23, 2010, vol. 58, No. 5, pp. 1474-1482.
Armstrong, M., Interview—Fractyl aims at the root of diabetes, Evaluate Vantage, Dec. 14, 2015, 2 pages.
Au Radiation Protection and Nuclear Safety Agency, "Exposure of Humans to Ionizing Radiation for Research Purposes—Code of Practice," May 2005, 36 pages.
Bakheet et al., "Endoluminal bariatric and metabolic therapies: state-of-the-art," Current Opinion in Gastroenterology, Sep. 2023, vol. 39, No. 5, pp. 362-369.

(56) References Cited

OTHER PUBLICATIONS

Ball et al., "Irreversible Electroporation A New Challenge in "Out of Operating Theater," Anesthesia," Anesthesia & Analgesia, May 2010, vol. 110, No. 5, pp. 1305-1309.
Benov et al., "Oxidative Damage of the Membrane Lipids after Electroporation," Gen. Physiol. Biophys., Apr. 4, 1994, vol. 13, pp. 85-97.
Bhonsle et al., "Mitigation of impedance changes due to electroporation therapy using bursts of high-frequency bipolar pulses," Dec. 2015, Biomed Eng Online, vol. 14, No. S3. pp. 1-4.
Bilska er al., "Theoretical modeling of the effects of shock duration, frequency, and strength on the degree of electroporation," Bioelectrochemistry, Jun. 1, 2000, vol. 51, No. 2, pp. 133-143.
Brethauer et al., "Gastrointestinal devices for the treatment of type 2 diabetes," Surgery for Obesity and Related Diseases, Jul. 2016, vol. 12, No. 6, pp. 1256-1261.
Busch et al., "Re-Cellularization Via Electroporation Therapy (RECET) Combined With GLP-1RA To Replace Insulin Therapy in Patients With Type 2 Diabetes 6 Months Results of the Eminent Study," Gastrointestinal Endoscopy, Jun. 1, 2023, vol. 97, No. 6, AB298, 1 page.
Busko, "Duodenal Mucosal Resurfacing Shows Early Promise in Diabetes," Medscape, Jun. 12, 2016, 3 pages.
Cassanelli et al., "Alteration of Membrane Permeability of Bacteria and Yeast by High Frequency Alternating Current (HFAC) ," The Open Microbiology Journal, Apr. 4, 2008, vol. 2, pp. 32-37.
Chang et al., "High efficiency gene transfection by electroporation using a radio-frequency electric field," Biochim Biophys Acta (BBA)-Molecular Cell Research, Apr. 17, 1991, vol. 1092, No. 2, pp. 153-160.
Chathadi et al., "The role of endoscopy in ampullary and duodenal adenomas," Gastrointest Endosc., Nov. 2015, vol. 82, No. 5, pp. 773-781.
Cherrington et al., "Hydrothermal Duodenal Mucosal Resurfacing: Role in the Treatment of Metabolic Disease," Gastrointest Endosc Clin N Am., Apr. 2017, vol. 27, No. 2, pp. 299-311.
ClinicalTrials.gov, "Evaluation of Duodenal Mucosal Resurfacing in Subjects With Type 2 Diabetes," [database online], published Apr. 10, 2014, last updated Feb. 14, 2024, 16 pages, retrieved Apr. 18, 2024, retrieved online: https://clinicaltrials.gov/study/NCT02413567.
Daskalov et al., "Exploring new instrumentation parameters for electrochemotherapy. Attacking tumors with bursts of biphasic pulses instead of single pulses," IEEE Engineering in Medicine and Biology Magazine, Jan.-Feb. 1999, vol. 18, No. 1, pp. 62-66.
Davalos et al., "Tissue ablation with irreversible electroporation, " Annals of Biomedical Engineering, Feb. 2005, vol. 33, pp. 223-231.
Dotsinksy et al., "New Modality for Electrochemotherapy of Surface Tumors," Biotechnology and Biotechnological Equipment, Apr. 16, 2014, vol. 26, No. 6, pp. 3402-3406.
Fractyl Health, "First Patients Enrolled in Multicenter Clinical Trial of Fractyl Revita DMR System," Press Release from Fractyl Health, Jul. 16, 2015, 2 pages.
Fractyl Health, "Fractyl Labs Announces Approval to Initiate Multicenter Clinical Trial of Revita DMR Procedure," Press Release from Fractyl Health, Jan. 12, 2015, 1 page.
Gehl et al., "In vivo electroporation of skeletal muscle: threshold, efficacy and relation to electric field distribution," Biochimica et Biophysica Acta (BBA)-General Subjects, Aug. 5, 1999, vol. 1428, Nos. 2-3, pp. 233-240.
Gianulis et al., "Electroporation of mammalian cells by nanosecond electric field oscillations and its inhibition by the electric field reversal." Sci Rep, Sep. 8, 2015, vol. 5, No. 13818, 10 pages.
Goldberg et al., "Towards Electroporation Based Treatment Planning Considering Electric Field Induced Muscle Contractions," Technology in Cancer Research and Treatment, Apr. 2, 2012, vol. 11, No. 2, pp. 189-201.
Grikscheit et al., "Tissue-engineered small intestine improves recovery after massive small bowel resection," Ann Surg., Nov. 1, 2004, vol. 240, No. 5, pp. 748-754.
Hibino et al., "Time courses of cell electroporation as revealed by submicrosecond imaging of transmembrane potential," Biophysical Journal, Jun. 1, 1993, vol. 64, No. 6, pp. 1789-1800.
Hofmann et al., "Electrochemotherapy: Transition from Laboratory to the Clinic," IEEE Engineering in Medicine and Biology, Nov./Dec. 1996, pp. 124-132 (Abstract only).
Hollerbach et al., "The EndoRotor®: endoscopic mucosal resection system for non-thermal and rapid removal of esophageal, gastric, and colonic lesions: initial experience in live animals," Endoscopy International Open, Apr. 2016, vol. 4, No. 4, E475-9.
International Preliminary Report on Patentability for International Application No. PCT/US2022/025630 dated Nov. 2, 2023, 8 pages.
International Preliminary Report on Patentability for International Application No. PCT/US2022/049653 mailed May 23, 2024, 8 pages.
Kaufman et al., "Society of Interventional Radiology Clinical Practice Guideline for Inferior Vena Cava Filters in the Treatment of Patients with Venous Thromboembolic Disease," JVIR, Oct. 2020, vol. 31, No. 10, pp. 1529-1544.
Kekez et al., "Contribution to the biophysics of the lethal effects of electric field on microorganisms," Biochemica et Biophysica Acta (BBA)-Biomembranes, Jan. 12, 1996, vol. 1278, No. 1, pp. 79-88.
Kotnok et al., "Cell membrane electropermeabilization by symmetrical bipolar pulses. Part I. Increased efficiency of permeabilizartion," Bioelectrochemistry. Aug. 1, 2001, vol. 54, No., 1, pp. 91-95.
Lavee et al., "A Novel Nonthermal Energy Source for Surgical Epicardial Atrial Ablation: Irreversible Electroporation," Heart Surg Forum, Mar. 2007, vol. 10, No. 2, E162-E167.
Li et al, "The Effects of Irreversible Electroporation (IRE) on Nerves," PLoS ONE, Apr. 14, 2011, vol. 6, No. 4, e18831, 7 pages.
Lissidini et al., "Emergency pancreaticoduodenectomy: When is it needed? A dual non-trauma centre experience and literature review," International Journal of Surgery, Sep. 2015, vol. 21, Supp. 1, pp. S83-S88.
Maor et al., "Endovascular Nonthermal Irreversible Electroporation: A Finite Element Analysis," J Biomech Eng., Mar. 2010, vol. 132, No. 3, 7 pages.
Maor et al., "Irreversible Electroporation Attenuates Neointimal Formation After Angioplasty," IEEE Transactions on Biomedical Engineering, Sep. 2008, vol. 55, No. 9, pp. 2268-2274.
Mathus-Vliegan et al., "Endobarrier: a unique but still premature concept," Nederlands Tijdschrift Voor Geneeskunde, Jan. 1, 2012, vol. 156, No. 13, A4590, 1 page.
Miklavcic et al., "The effect of high frequency electric pulses on muscle contractions and antitumor efficiency in vivo for a potential use in clinical electrochemotherapy," J Bioelectrochemistry, Feb. 2005, vol. 65, No. 2, pp. 121-128.
Miklovic et al., "A Comprehensive Characterization of Parameters Affecting High-Frequency Irreversible Electroporation Lesions," Ann. Biomed Eng., Jul. 2017, vol. 45, pp. 2524-2534.
Miyawaki et al., "Inhibition of gastric inhibitory polypeptide signaling prevents obesity," Nat Med., Jul. 2002, vol. 8, No. 7, pp. 738-742.
Neto et al., "Endoscopic Duodenal Mucosal Resurfacing Improves Glycemic and Hepatic Parameters in Patients With Type 2 Diabetes: Data From a First-in-Human Study," Gastroenterology, Apr. 2016, vol. 150, No. 4, Supp. 1, 1 page.
Neto, "Duodenum resurfacing procedure improved type 2 diabetes markers," Endocrine Today, Oct. 2014, vol. 12, Iss. 10, 2 pages.
Non-Final Office Action in U.S. Appl. No. 17/076,692, mailed Aug. 15, 2024, 17 pages.
Patel et al., "Endoscopic ampullectomy: techniques and outcomes," Journal of Clinical Gastroenterology, Jan. 1, 2012, vol. 46, No. 1, pp. 8-15.
Pemberton et al., "High-frequency electroporation and maintenance of pUC- and pBR-based cloning vectors inPseudomonas stutzeri," Current Microbiology, Jul. 1992, vol. 25, pp. 25-29.
Rodriguez et al., "O.145 Duodenal Mucosal Resurfacing (DMR)-A New Endoscopic Treatment for Type 2 Diabetes (T2DM) a Safety and Proof-Of-Principle Cohort Study," Abstract from the 19th World Congress of the International Federation for the Surgery of Obesity & Metabolic Disorders (IFSO) Montreal, CA, Aug. 26-30, 2014, 1 page.

(56) References Cited

OTHER PUBLICATIONS

Rodriguez, L. et al., "Type 2 diabetes: Renew duodenal mucosa with thermal ablation," Med Online, May 25, 2015, retrieved online at https://medonline.at/news/uncategorized/162382/typ-2-diabetes-thermal-ablation/, 3 pages.

Rowan et al., "Pulsed electric field inactivation of diarrhoeagenic Bacillus cereus through irreversible electroporation," Letters in Applied Microbiology, Aug. 1, 2000, vol. 31, No. 2, pp. 110-114.

Rubino et al., "Potential of surgery for curing type 2 diabetes mellitus," Ann Surg. Nov. 2002, vol. 236, No. 5, pp. 554-559.

Rubino, F et al., "Metabolic Surgery in the Treatment Algorithm for Type 2 Diabetes: A Joint Statement by International Diabetes Organizations," Diabetes Care, May 13, 2016, vol. 39, No. 6, pp. 861-877.

Rubinsky et al., "Irreversible Electroporation: A New Ablation Modality—Clinical Implications," Technology in Cancer Research and Treatment, Feb. 2007, vol. 6, No. 1, pp. 37-48.

Rubinsky et al., "Optimal Parameters for the Destruction of Prostate Cancer Using Irreversible Electroporation," J Urol., Dec. 2008, vol. 180, No. 6, pp. 2668-2674.

Sarria et al., "Morphometric study of the layers of the canine small intestine at five sampling sites," Veterinary Journal, Jun. 1, 2012, vol. 192, No. 3, pp. 498-502.

Sartoretto et al., "Duodenal Mucosal Regeneration Induced By Endoscopic Pulsed Electric Field Treatment Improves Glycemic Control in Patients With Type II Diabetes—Interim Results From a First-In-Human Study," Endoscopic Technology, Jun. 2023, vol. 97, Issue 6, Supp. AB704-AB705.

Scuderi et al., "The use of high-frequency short bipolar pulses in cisplatin electrochemotherapy in vitro," Radiology & Oncology, Jun. 2019, vol. 53, No. 2, pp. 194-205.

Semkova et al., "Autologous transplantation of genetically modified iris pigment epithelial cells: A promising concept for the treatment of age-related macular degeneration and other disorders of the eye," Proceedings of the National Academy of Sciences, Oct. 1, 2002, vol. 99, No. 20, pp. 13090-13095.

Sen et al., "Autologous transplantation of endothelial progenitor cells genetically modified by adeno-associated viral vector delivering insulin-like growth factor-1 gene after myocardial infarction," Hum Gene Ther., Oct. 2010, vol. 21, No. 10, pp. 1327-1334.

Tolman et al., "Spectrum of liver disease in type 2 diabetes and management of patients with diabetes and liver disease," Diabetes Care, Mar. 1, 2007, vol. 30, No. 3, pp. 734-743.

Tomizawa et al., "Clinical Outcome of Endoscopic Mucosal Resection (EMR) of Sporadic, Non-Ampullary Duodenal Adenoma (SNADA): Predictor Analysis of Safety and Efficacy From a High Volume U.S. Tertiary Referral Center," Gastrointestinal Endoscopy, May 1, 2017, vol. 85, Issue 5, Supplement, p. AB72, 1 page.

Tovar et al., "Electroporation and recovery of cardiac cell membrane with rectangular voltage pulses," American Journal of Physiology-Heart and Circulatory Physiology, Oct. 1992, vol. 263, No. 4, pp. H1128-H1136.

Tsiamoulos et al., "Endoscopic mucosal ablation: a novel technique for a giant nonampullary duodenal adenoma," Endoscopy, Dec. 2013, vol. 45, No. 2, pp. E12-E13.

Tyurin et al., "Electrotransformation of Clostridium acetobutylicum ATCC 824 using high-voltage radio frequency modulated square pulses," J App. Microbio., Feb. 1, 2000, vol. 88, No. 3, pp. 220-227.

Van Baar et al., "Alternative treatments for type 2 diabetes and associated metabolic diseases: medical therapy or endoscopic duodenal mucosal remodelling?" Gut, Nov. 1, 2021, vol. 70, No. 11, pp. 2196-2204.

Van Baar et al., "Single Catheter for Duodenal Mucosal Resurfacing Demonstrates Similar Safety Profile with Improved Procedure Time when Compared to Original Dual Catheter: Multicenter Study of Subjects with Type 2 Diabetes," Gastroenterology, Apr. 2017, vol. 152, Issue 5, Supplement 1, p. S825. 1 page.

Wong et al., "Approaches to endoscopic ampullectomy," Current Opinions in Gastroenterology, Sep. 2004, vol. 20, No. 5, pp. 460-467.

Yuan et al., "835-P: First-in-Human Duodenal Endoscopic Recellularization via Electroporation Therapy for Type 2 Diabetes—An Interim Report," Clinical Therapeutics, Jun. 20, 2023, vol. 72, Supp. 1, p. 835.

Zald et al., "Improved Transfection Efficiency of 293 Cells by Radio Frequency Electroporation," Biotechniques, Mar. 2000, vol. 28, No. 3, pp. 418-420.

Zimmerman, D. et al., "Endoscopy jumps the boundaries," Healthcare in Europe, Jul. 1, 2015, retrieved online at https://healthcare-in-europe.com/en/news/endoscopy-jumps-the-boundaries.html, 6 pages.

Non-Final Office Action in U.S. Appl. No. 17/725,449, by D'Agostino et al., mailed Aug. 30, 2024, 18 pages.

* cited by examiner

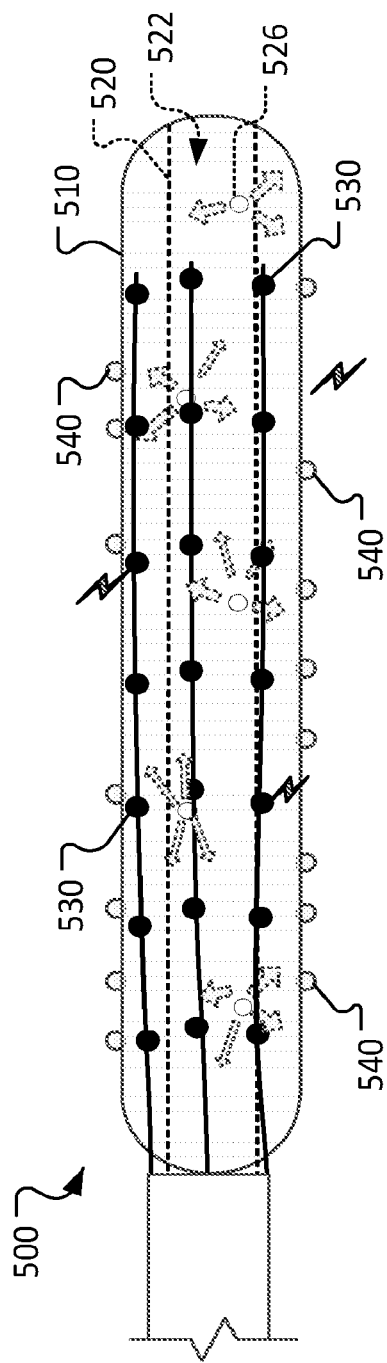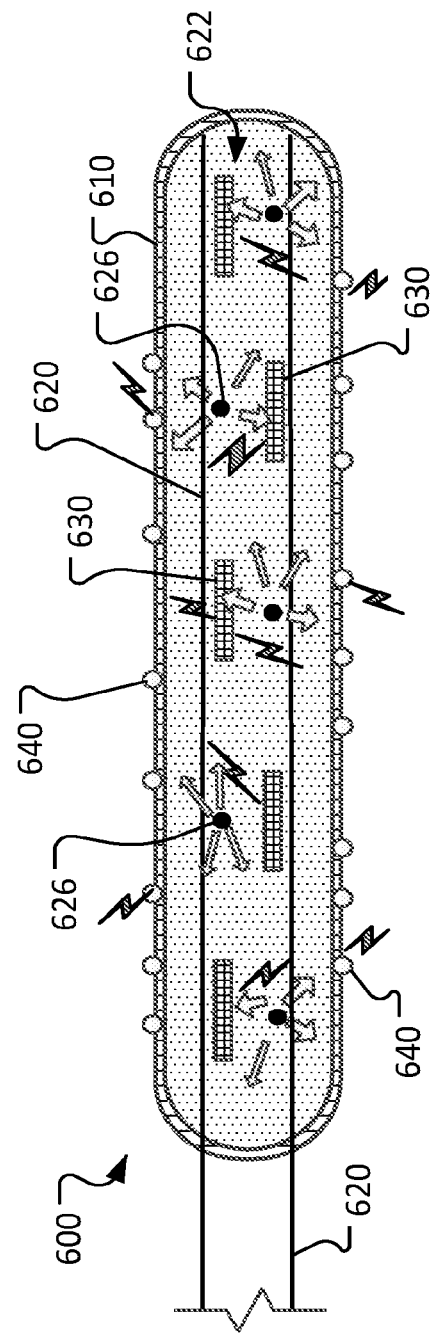

ELECTROPORATION FOR OBESITY OR DIABETES TREATMENT

CROSS-REFERENCE TO RELATED APPLICATIONS

This application is a continuation of U.S. application Ser. No. 15/766,604, filed Apr. 6, 2018, now issued as U.S. Pat. No. 11,337,749, which is a National Stage application under 35 U.S.C. § 371 of International Application No. PCT/US2016/055966, having an International Filing Date of Oct. 7, 2016, which claims the benefit of U.S. Provisional Application Ser. No. 62/238,191, filed on Oct. 7, 2015, the entire disclosures of each which are incorporated herein by reference in their entirety.

BACKGROUND

1. Technical Field

This document relates to devices and methods for the treatment of health conditions including obesity and diabetes. For example, this document relates to devices and methods for treating obesity and diabetes using electroporation endoscopically.

2. Background Information

Obesity is a global problem crossing age, ethnic, and socioeconomic boundaries. In general, obesity means having too much body fat. Morbid obesity is a serious health condition that can interfere with basic physical functions such as breathing or walking. Individuals who are morbidly obese are at greater risk for illnesses including diabetes, high blood pressure, sleep apnea, gastroesophageal reflux disease, infertility, low back pain, asthma, gallstones, osteoarthritis, heart disease, and cancer. Billions of dollars are spent each year treating millions of individuals around the world suffering from such diseases. Many people suffering from morbid obesity find it nearly impossible to lose weight by controlling their diet and exercising.

Type 2 diabetes is a chronic condition that affects the way a body metabolizes sugar (glucose). With type 2 diabetes, the body either resists the effects of insulin a hormone that regulates the movement of sugar into cells—or doesn't produce enough insulin to maintain a normal glucose level. More common in adults, type 2 diabetes increasingly affects children as childhood obesity increases. There is no known cure for type 2 diabetes. In some cases it may be managed by eating well, exercising and maintaining a healthy weight. If diet and exercise aren't enough to manage blood sugar well, diabetes medications or insulin therapy may be needed.

Ablation/electroporation therapy is a type of minimally invasive procedure used to destroy tissue associated with various conditions. For example, ablation procedures can be used to treat tumors or to destroy heart tissue that's causing abnormally rapid heart rhythms. Ablation therapy may be administered using probes inserted through the skin, flexible tubes (catheters) inserted through a body conduit, or energy beams to reach the area being treated. Imaging techniques may be used to guide the ablation. The tissue is injured or destroyed with heat (e.g., radiofrequency ablation), extreme cold (cryoablation), lasers or a chemical.

SUMMARY

This document provides devices and methods for the treatment of health conditions including obesity and diabetes. In some embodiments, the methods and systems provided herein can cause weight loss or control diabetes by reducing the caloric absorption of an individual, by increasing levels of gut hormones important in appetite regulation and insulin secretion, and/or by reshaping the mucosa of the small intestines. For example, this document provides several devices and methods for treating obesity and diabetes by using electroporation to modulate the duodenal mucosa. In addition, this document provides devices and methods for bypassing portions of the gastrointestinal (GT) tract to reduce nutritional uptake.

In one implementation, an electroporation device includes a shaft defining a first lumen therethrough; a proximal balloon circumferentially attached about a distal portion of the shaft; a middle portion extending distally of the proximal balloon; and a distal balloon extending distally of the middle portion. The middle portion defines a middle portion lumen in communication with the first lumen. The middle portion includes one or more electrodes configured to administer electroporation energy. The middle portion includes one or more apertures through a wall of the middle portion and in communication with the middle portion lumen. The middle portion has a longitudinally contracted configuration and a longitudinally extended configuration that is longer than the longitudinally contracted configuration. In some embodiments, the middle portion has a fixed length.

Such an electroporation device may optionally include one or more of the following features. The distal balloon may have a distal balloon lumen therethrough that is in communication with the middle portion lumen. The distal balloon lumen may be defined by a distal shaft on which the distal balloon is circumferentially attached. The shaft may define a proximal balloon inflation lumen in communication with the proximal balloon. The shaft and the middle portion may define a distal balloon inflation lumen in communication with the distal balloon. The middle portion may comprise an accordion configuration that facilitates the middle portion to reconfigure between the longitudinally contracted configuration and the longitudinally extended configuration. The first lumen and the middle portion lumen may be configured to receive an endoscope or to advance through the working channel of an endoscope. This catheter can also be advanced over a guide wire under endoscopic and/or fluoroscopic guidance.

In another implementation, a method of administering electroporation energy to patient includes deploying an electroporation device at a target location within the patient, energizing the one or more electrodes with electroporation energy, and, while energizing the one or more electrodes, supplying electrically conductive liquid into the electroporation device such that the electrically conductive liquid flows through the one or more apertures. The electroporation device includes a shaft defining a first lumen therethrough; a proximal balloon circumferentially attached about a distal portion of the shaft; a middle portion extending distally of the proximal balloon; and a distal balloon extending distally of the middle portion. The middle portion defines a middle portion lumen in communication with the first lumen. The middle portion includes one or more electrodes configured to administer electroporation energy. The middle portion includes one or more apertures through a wall of the middle portion and in communication with the middle portion lumen. The middle portion has a longitudinally contracted configuration and a longitudinally extended configuration that is longer than the longitudinally contracted configuration. In some embodiments, the middle portion has a fixed length.

Such a method of administering electroporation energy to patient may optionally include one or more of the following features. The target location may be a duodenum or a jejunum. The method may further comprise, before supplying electrically conductive liquid into the electroporation device, inflating the proximal balloon and the distal balloon. The method may further comprise, before supplying electrically conductive liquid into the electroporation device, extending the middle portion to reconfigure the middle portion from the longitudinally contracted configuration to the longitudinally extended configuration. The electrically conductive liquid may carry the electroporation energy from the one or more electrodes to tissue of the patient. The method may further comprise installing an endoscope shaft into the first lumen and the middle portion lumen, and using a single or double channel endoscope to deploy the electroporation device and or inject the electrically conductive liquid. This catheter can also be advanced over a guide wire under endoscopic and/or fluoroscopic guidance.

In another implementation, an electroporation device includes a shaft defining a lumen therethrough; a balloon circumferentially attached about a distal portion of the shaft, wherein the balloon has a longitudinal length between 5 to 20 cm; and one or more electrodes disposed on an outer surface of the balloon. The lumen is configured to receive an endoscope therein. In some embodiments, the balloon is a porous material that facilitates passage of an electrically conductive liquid therethrough. This catheter can also be advanced over a guide wire under endoscopic and/or fluoroscopic guidance.

In another implementation, a method of treating a patient includes deploying an electroporation device at a target location within an intestine of the patient. The electroporation device includes a shaft defining a first lumen therethrough; a distal balloon circumferentially attached about a distal portion of the shaft; a middle portion extending proximal to the distal balloon, where the electroporation electrodes are mounted; and an overtube with proximal balloon delivered over a single or double channel endoscope capable of inflating and deflating separate from distal balloon. The electroporation catheter is advanced through the working channel of the single or double channel endoscope to deliver therapy to the target tissue. The inflated distal balloon on the electroporation catheter and the inflated proximal balloon on the overtube over the endoscope provide a seal to create a column of electrically conductive liquid injected through the working channel of the endoscope.

In another implementation, a method of treating a patient includes deploying an electroporation device at a target location within an intestine of the patient. The electroporation device/catheter includes a shaft defining a first lumen therethrough, with no balloon on this shaft just electrodes delivered through the working channel of a single of double channel endoscope. An overtube with two balloons (proximal and distal) separated by a tissue supporting structure to spread the duodenal or jejunal folds is delivered over a single or double channel endoscope to the target small intestinal segment. The endoscope is retracted from the distal overtube balloon and a self sealing valve in the lumen of the distal portion of the overtube/distal balloon is sealed. After the proximal balloon is inflated and electrically conductive liquid is injected through the working channel of the endoscope to create a liquid column. The electroporation catheter is then delivered through the endoscope into the liquid column to deliver the electroporation current. In one example, the tissue supporting structure can be a collapsible/ expandable stent or mesh, while in its expanded configuration the tissue supporting structure can spread mucosa folds to increase the surface area of mucosa that is accessible and exposed to the conductive liquid.

In another implementation, a method of treating a patient includes deploying an electroporation device at a target location within an intestine of the patient. The electroporation device includes a shaft defining a first lumen therethrough; a proximal balloon circumferentially attached about a distal portion of the shaft; a middle portion extending distally of the proximal balloon; and a distal balloon extending distally of the middle portion. The middle portion defines a middle portion lumen in communication with the first lumen. The middle portion includes one or more electrodes configured to administer electroporation energy. The middle portion includes one or more apertures through a wall of the middle portion and in communication with the middle portion lumen. The middle portion has a longitudinally contracted configuration and a longitudinally extended configuration that is longer than the longitudinally contracted configuration.

Such a method of treating a patient may optionally include one or more of the following features. The method may further comprise energizing the one or more electrodes with electroporation energy. The method may further comprise supplying liquid into the electroporation device such that the liquid flows through the one or more apertures and into the intestine. The liquid may comprise medicinal solutions or drugs. The method may further comprise stretching at least a portion of the intestine to increase an intestinal surface area in contact with the liquid.

Such a method of treating a patient may optionally include one or more of the following features. The liquid may comprise medicinal solutions or drugs that can be delivered to target small intestinal cell through the process of reversible electroporation. The method may further comprise stretching at least a portion of the intestine to increase an intestinal surface area in contact with the liquid. The method may further comprise an over the scope overtube with tissue retraction structure in between two balloons delivered over an endoscope to create a liquid column with stretch intestinal surface to effectively deliver electroporation current through a catheter delivered through the working channel of the endoscope. Finally, any of the electroporation catheters described can also be delivered over a guidewire under fluoroscopic guidance.

Particular embodiments of the subject matter described in this document can be implemented to realize one or more of the following advantages. In some embodiments, methods and systems provided herein provide a minimally invasive weight loss and/or diabetes therapy. For example, in some embodiments electroporation of the duodenal mucosa is performed endoscopically. Such minimally invasive techniques can reduce recovery times, patient discomfort, and treatment costs. In some embodiments, the methods and systems provided herein alter the body's ability to process sugar and may improve glycemic control for patients with Type 2 diabetes. Additionally, these catheters and/or overtubes can be used to ablate other portions of the gastrointestinal tract where superficial mucosal ablation can be utilized such as in the treatment of metaplasia, dysplasia, or superficial neoplasia of the gastrointestinal tract and/or cystic neoplasms of the pancreas where the electroporation catheter with electrodes is delivered through a 19 gauge endoscopic ultrasound needle to the cyst under endosonographic guidance.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIG. 5 is a plan view of another device for administering electroporation to a GI tract (e.g., duodenum) in accordance with some embodiments provided herein. The device is shown in an expanded configuration.

FIG. 6 is a plan view in longitudinal cross-section of another device for administering electroporation to a GI tract (e.g., duodenum) in accordance with some embodiments provided herein. The device is shown in an expanded configuration.

Like reference numbers represent corresponding parts throughout.

DETAILED DESCRIPTION

This document provides devices and methods for the treatment of health conditions including obesity and diabetes. In some embodiments, the methods and systems provided herein can cause weight loss and/or can control diabetes by reducing the caloric absorption of an individual, by increasing levels of gut hormones important in appetite regulation and insulin secretion, and/or by reshaping the mucosa of the small intestines. For example, this document provides several devices and methods for treating obesity and diabetes by using electroporation to modulate the duodenal mucosa. In addition, this document provides devices and methods for bypassing portions of the GI tract to reduce nutritional uptake.

Figure 1:
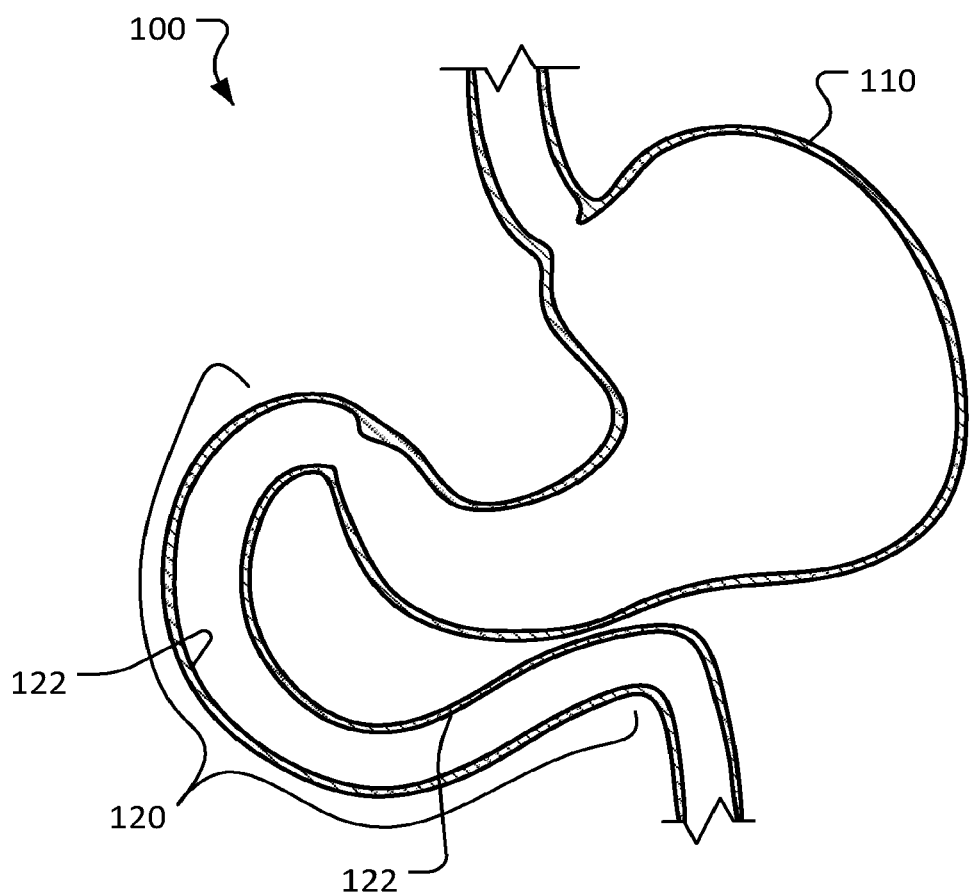
FIG. 1 is a cross-sectional view of a portion of a human GI tract, including a stomach and duodenum.

Referring to FIG. 1, a human GI tract portion 100 includes a stomach 110 and a duodenum 120. The lining of duodenum 120 is made up of duodenal mucosa 122. Duodenal mucosa 122 is made up of short tubular invaginations called crypts, where intestinal stem-cells (cells that can differentiate to a different cell type) and paneth cells (cells that fuel the activity of stem cells) reside. Duodenal mucosa 122 also includes villi, where enterocytes (columnar epithelium consisting of one layer of tall rectangular cells concerned with absorbing nutrients from the gut); goblet cell (cells that produce alkaline mucus to protect the small intestines); and enteroendocrine cells (specialized endocrine cells of the gastrointestinal tract that produce gastrointestinal hormones important for digestion and glucose control) reside.

As described further below, devices and methods for administering electroporation to modulate the duodenal mucosa 122 are provided herein. Moreover, using the provided devices and methods for administering electroporation, the depths and cell composition of the crypts and villi of duodenal mucosa 122 can be modulated. Using such devices and techniques, weight loss and/or control of diabetes by reducing the caloric absorption, by increasing gut hormones, and/or by re-setting the diseased intestinal mucosa of an individual can be achieved.

Figure 2:
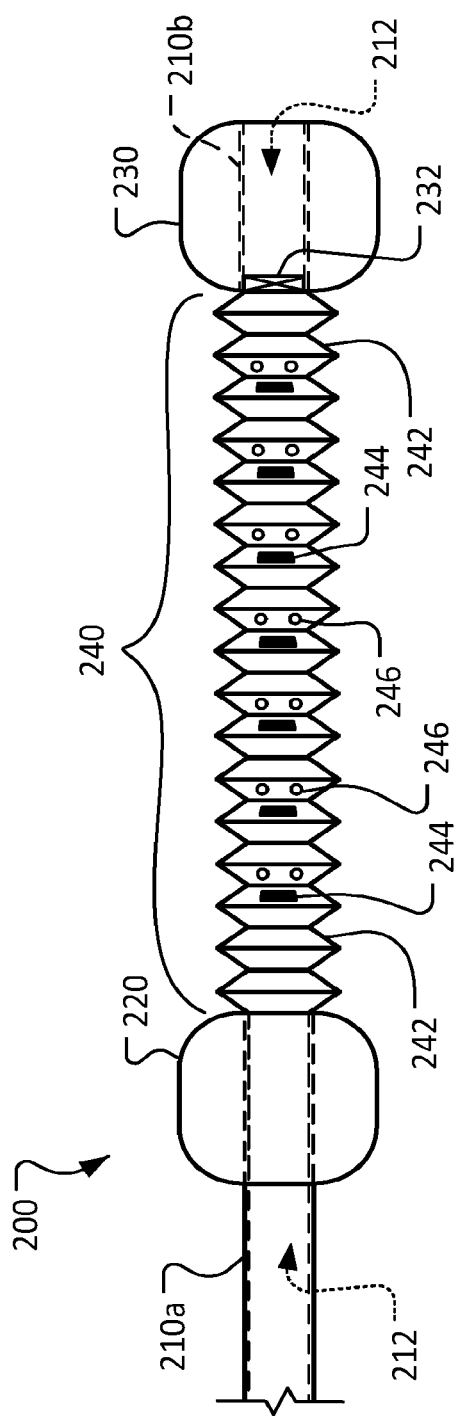
FIG. 2 is a plan view of a device for administering electroporation to a GI tract (e.g., duodenum) in accordance with some embodiments provided herein. The device is shown in an expanded configuration.

Referring to FIG. 2, an example mucosa electroporation device 200 includes a proximal shaft 210a, a proximal balloon 220, a distal balloon 230, a distal shaft 210b, and a middle portion 240. Proximal balloon 220 is attached to proximal shaft 210a in a circumferential fashion. Middle portion 240 is attached to proximal shaft 210a and extends distally from proximal shaft 210a. The distal end of middle portion 240 is attached to distal shaft 210b. Distal balloon 230 is attached to distal shaft 210b in a circumferential fashion.

Proximal shaft 210a, middle portion 240, and distal shaft 210b define a lumen 212. In some embodiments, lumen 212 is sized to slidably receive an endoscope shaft. In some embodiments, lumen 212 is sized to slidably receive a guidewire.

Proximal balloon 220 and distal balloon 230 are inflatable members. Accordingly, inflation media (e.g., saline, water, $CO_2$, air, etc.) can be supplied to proximal balloon 220 and distal balloon 230 to cause their inflation. In some embodiments, the wall of proximal shaft 210a defines an inflation lumen through which inflation media is supplied to proximal balloon 220. In some embodiments, (i) the wall of proximal shaft 210a, (ii) the wall of middle portion 240, and (iii) the wall of distal shaft 210b defines an inflation lumen through which inflation media is supplied to distal balloon 230. Accordingly, in some embodiments the inflation and deflation of proximal balloon 220 and distal balloon 230 can be controlled separately. Alternatively, in some embodiments the inflation and deflation of proximal balloon 220 and distal balloon 230 are controlled unitarily. While balloons 220 and 230 are deflated, in some embodiments mucosa electroporation device 200 can pass through the working channel of an endoscope.

Proximal balloon 220 and distal balloon 230 are flexible, elastic, conformable balloon members. In some embodiments, proximal balloon 220 and distal balloon 230 are made from silicone, or latex, or other types compliable materials. Accordingly, when inflated, proximal balloon 220 and distal balloon 230 are conformable to the topography of the GI conduit. Therefore, proximal balloon 220 and distal balloon 230, when inflated, provide a substantial seal against the wall of the GI conduit. While in some embodiments proximal balloon 220 and distal balloon 230 are made from the same material, in some embodiments proximal balloon 220 and distal balloon 230 are made from dissimilar materials.

In some embodiments, the maximum outer diameter of proximal balloon 220 and/or distal balloon 230, when inflated, is in a range from about 30 mm to about 50 mm. The maximum inflated outer diameter of proximal balloon 220 and distal balloon 230 is scalable to any suitable size. For example, in some embodiments the maximum outer diameter of proximal balloon 220 and/or distal balloon 230, when inflated, is in a range from about 35 mm to about 45 mm, or from about 40 mm to about 50 mm, or from about 30 mm to about 40 mm, or from about 25 mm to about 35 mm, or from about 30 mm to about 60 mm. In some embodiments, the maximum outer diameters of proximal balloon 220 and distal balloon 230 are equal to each other. In some embodiments, the maximum outer diameters of proximal balloon 220 and distal balloon 230 are unequal.

As described further below, distal shaft 210b or distal balloon 230 includes a valve 232 disposed within the lumen 212. Valve 232 allows passage of an instrument (e.g., an endoscope or guidewire) therethrough. But, when no such instrument is in contact with valve 232, valve 232 acts as a closure at the distal end of lumen 212 so that lumen 212 is dead ended at or near distal balloon 230.

Middle portion 240 is longitudinally extendable and laterally deflectable and flexible. In the depicted embodiment, middle portion 240 is configured as an accordion member having multiple pleats and multiple flexible, extendable portions 242. In some embodiments, middle portion 240 is configured in other arrangements that are longitudinally extendable and laterally flexible. For example, and without limitation, in some embodiments middle portion 240 is configured as a coil (e.g., helically), an elastic member, an inter-foldable member, a rolled-up member, a telescoping member, and the like, and combinations thereof.

In some embodiments, middle portion 240, when fully longitudinally extended, is about 30 cm in length. The fully longitudinally extended length of middle portion 240 is scalable to any suitable size. For example, in some embodiments the fully longitudinally extended length of middle portion 240 is in a range from about 25 cm to about 35 cm, or from about 30 cm to about 40 cm, or from about 20 cm to about 30 cm, or from about 15 cm to about 35 cm, or from about 25 cm to about 50 cm.

Middle portion 240 is configured to facilitate electroporation. Accordingly, middle portion 240 includes one or more electrodes 244. Electrodes 244 can be different types of electrodes, and/or electrodes 244 can be configured to deliver different types of energy in different embodiments of electroporation device 200. For example, in the depicted embodiment electrodes 244 are DC electrodes. Alternatively, or additionally, mucosa electroporation device 200 can be configured to deliver other types of electroporation energy such as, but not limited to, radiofrequency (RF), AC, cryogenic, chemical, and the like. In some embodiments, a combination of such energy sources can be used within a single embodiment of electroporation device 200 (e.g., RF and DC are used in combination is some embodiments). The electroporation energy can be monopolar or bipolar. Electrodes 244 can be electrically wired to an electroporation energy source (not shown) located external to the patient. In some implementations, two or more types of electroporation energy sources can be coupled to electrodes 244. For example, in one particular non-limiting implementation a RF source and a NANOKNIFE® irreversible electroporation system by AngioDynamics, Inc. are both coupled to electrodes 244 such that a switch box is used to select between the two sources of energy.

Middle portion 240 also includes one or more apertures 246. Apertures 246 are openings through the wall of middle portion 240 such that lumen 212 is in fluid communication with the exterior of electroporation device 200 via apertures 246. In some embodiments, alternatively or additionally, the material comprising middle portion 240 is porous such that lumen 212 is in fluid communication with the exterior of mucosa electroporation device 200 via the pores of the material. As described further below, apertures 246 can provide passageways for a conductive liquid that will carry electroporation energy from electrodes 244 to the wall of the tissue structure (e.g., the duodenum) in which electroporation device 200 is resident.

Figure 3:
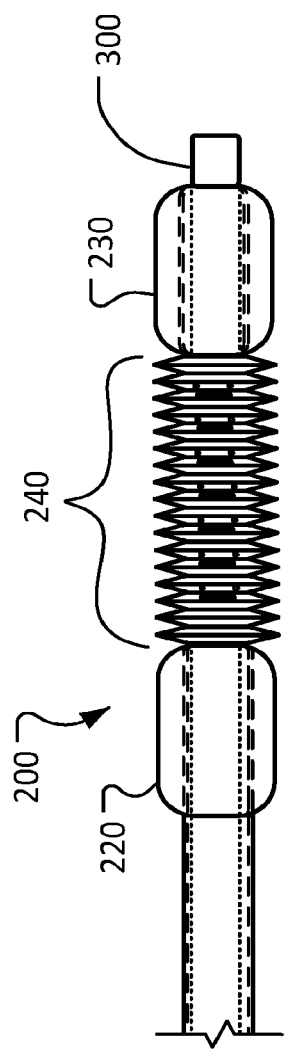
FIG. 3 is a plan view of the device of FIG. 2 shown in a contracted delivery configuration.

Referring also to FIG. 3, in some embodiments electroporation device 200 can be configured in a contracted configuration for minimally invasive deployment into the GI tract. For example, in the depicted arrangement electroporation device 200 is disposed over an endoscope 300 (only the distal end portion of endoscope 300 is illustrated), and electroporation device 200 is in a radially and longitudinally contracted configuration (as compared to the radially expanded and longitudinally extended configuration of FIG. 2). Endoscope 300 is disposed within lumen 212. Proximal balloon 220 and distal balloon 230 are deflated such that their outer diameters are reduced in comparison to their inflated outer diameters. Middle portion 240 is longitudinally contracted (as compared to the longitudinally extended configuration of FIG. 2). In this configuration, electroporation device 200 is configured to be endoscopically deployed within the GI tract of a patient using endoscope 300.

In some embodiments, electroporation device 200 is configured to be deployed via a working channel of an endoscope or laparoscope. In some embodiments, electroporation device 200 is configured to be deployed over a guidewire instead of over endoscope 300. One or more radiopaque markers or echogenic markers, or both, may be disposed on one or more locations or on one or more portions of electroporation device 200 (e.g., on the balloons 220 and/or 230).

Figure 4:
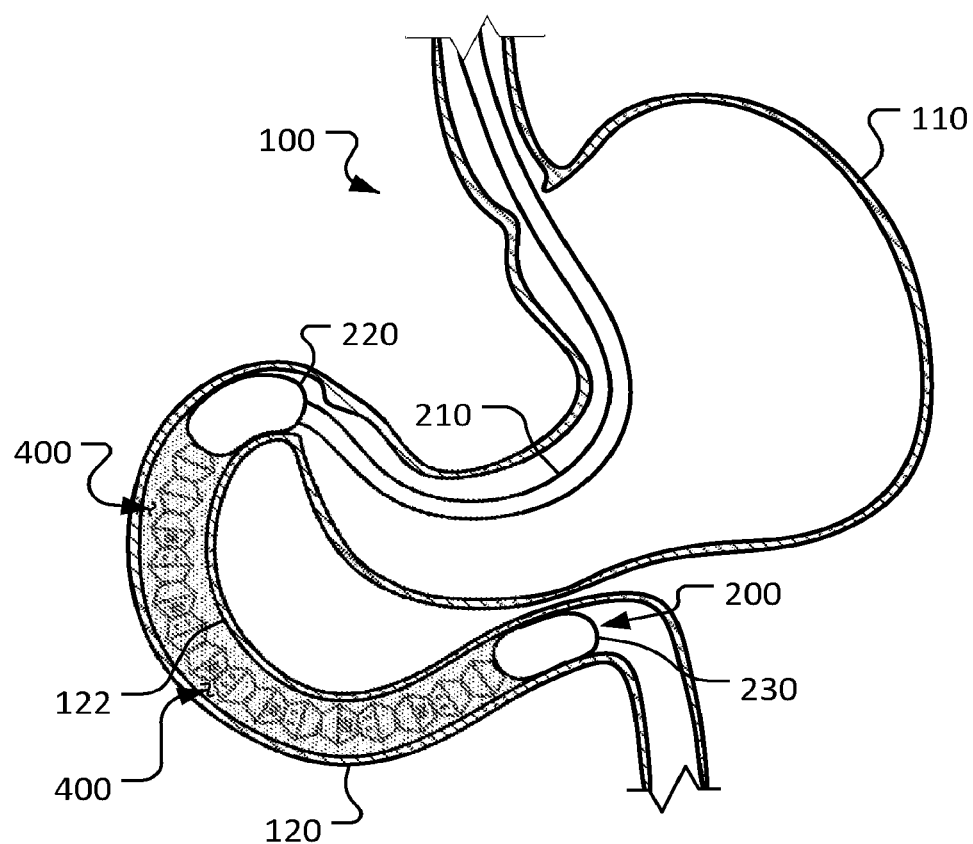
FIG. 4 shows the device of FIGS. 2 and 3 deployed in a duodenum in an arrangement where the device can provide an electroporation treatment to modulate the duodenal mucosa.

Referring to FIG. 4, electroporation device 200 can be deployed within duodenum 120 to provide electroporation treatments to a patient. Electroporation device 200 can treat obesity and diabetes using electroporation to modulate the duodenal mucosa 122.

Electroporation device 200 is shown after removal of a delivery device, such as endoscope 300 (FIG. 3). In some deployment techniques, endoscope 300 is used to position the distal balloon 230 in a desired location within duodenum 120 or distal small intestines (such as the jejunum). In some deployment techniques, electroporation device 200 is positioned within a working channel of an endoscope. Then, distal balloon 230 is inflated to temporarily fix distal balloon 230 in the desired location. Next, endoscope 300 is pulled back, proximally. In doing so, middle portion 240 is longitudinally extended and laterally deflected within duodenum 120. When proximal balloon 220 is positioned in a desired location within duodenum 120, then proximal balloon 220 is inflated to temporarily fix proximal balloon 220 in the desired location. Then, endoscope 300 can be further pulled back proximally (and may be completely disengaged from electroporation device 200.

When fully deployed, proximal balloon 220 is inflated to occlude the proximal portion of the duodenum 120, and distal balloon 230 is inflated to occlude the distal portion of duodenum 120. The interior space of duodenum 120 defined between the proximal balloon 220 and the distal balloon 230 is substantially sealed from other portions of the GI tract 100.

With the balloons 220, 230 inflated, an electrically conductive liquid 400 can be delivered into the interior space between the balloons 220, 230 by injecting it via lumen 212 and apertures 246 (refer to FIG. 2). In some implementations, saline is used for electrically conductive liquid 400. In some implementations, hypertonic saline is used for electrically conductive liquid 400. In some implementations, dextrose is used for electrically conductive liquid 400. Other types of electrically conductive liquid 400 can also be used. For example, conductive liquid 400 can include, but is not limited to, cation-rich solutions such as sodium ion, potassium ion, calcium ion, magnesium ion, etc., of varying concentrations, for example 3% sodium chloride, calcium chloride, calcium carbonate, potassium chloride, potassium carbonate, etc. In the same regard, ionized forms of known medicinal solutions or drugs may be infused into the interior space between the balloons 220, 230 to be placed intracellularly in target cells, such as the duodenal mucosa, both for stimulation, regeneration, and otherwise targeted therapies for obesity and diabetes. The electroporation and/or current source will serve as a vehicle for intracellular delivery and the electronic transfer of the electroporation energy is achieved by ionization of these solutions. In some implementations, a combination of different types of drugs and or other types of electrically conductive liquid 400 are used.

Electrodes 244 can be energized to provide a source of electroporation energy. The electrically conductive liquid 400 within the interior space between the balloons 220, 230 will carry the electrical energy from the electrodes 244 to duodenal mucosa 122. The pressure of electrically conductive liquid 400 within the interior space should be adjusted to be high enough such that electrically conductive liquid 400 is forced into the crypts of duodenal mucosa 122.

In some implementations, a sequential ablation technique where saline and dextrose are circulated in the interior space between the balloons 220, 230 sequentially, while delivering electroporation energy throughout is used. This would be a mechanical method to create phased ablation to minimize sloughing and essentially completely prevent bleeding or stricture. There would be a timed sequence with a pre-time set of two pumps that would create the phased delivery. The setup would be one pump continuously infuses the saline, and through the tubing a second pump will change the volume of dextrose or lactated ringers going in. The electroporation source could be kept constant, or alternatively more than one electrode placed along electroporation device 200 and a more standard electronic phasing circuit can be implemented.

In some embodiments, a hydrogel is used to electrically carry electroporation energy. In some cases the hydrogel may facilitate longer lasting contract of electroporation energy with duodenal mucosa 122, including within the crypts of duodenal mucosa 122.

In some embodiments, proximal balloon 220 is positioned so as to envelop the ampulla and to protect the ampulla during electroporation. Accordingly, in some embodiments proximal balloon 220 is highly compliant to provide such protection to the ampulla.

After administration of electroporation using electroporation device 200 and electrically conductive liquid 400, the delivery of the electroporation energy can be stopped. Then the balloons 220, 230 can be deflated, and electroporation device 200 can be removed from GI tract 100 of the patient.

Referring to FIG. 5, another example electroporation device 500 embodiment is illustrated. Electroporation device 500 includes a balloon 510, a shaft 520, and one or more electrodes 530. Balloon 510 is circumferentially disposed about shaft 520. Electrodes 530 are disposed on the outer surface of balloon 520.

Shaft 520 defines a lumen 522 that is analogous to lumen 212 of electroporation device 200. In some embodiments, shaft 520 also defines one or more apertures 526. Apertures 526 allow an electrically conductive liquid to flow from lumen 522 to an interior space of balloon 510. However, such electrically conductive liquid is optional. That is, in some embodiments electrodes 530 deliver electroporation energy to duodenal mucosa 122 without the use of electrically conductive liquid.

Balloon 510 can be made of the materials described above in reference to balloons 220, 230 of electroporation device 200, for example. In some embodiments, the longitudinal length of balloon 510 is about 15 cm. The longitudinal length of balloon 510 is scalable to any suitable size. For example, in some embodiments the longitudinal length of balloon 510 is in a range from about 10 cm to about 20 cm, or from about 15 cm to about 25 cm, or from about 10 cm to about 25 cm, or from about 15 cm to about 20 mm, or from about 10 cm to about 15 cm. Balloon 510 can have an inflated maximum outer diameter that is sized as described above in reference to balloons 220, 230 of electroporation device 200, for example.

In some embodiments, electroporation device 500 is an example of a weeping balloon design. That is, balloon 510 can be partly or fully made from a porous or microporous material such that an electrically conductive liquid can elute, weep, or be otherwise transmitted through balloon 510 to form droplets 540. Accordingly, droplets 540 of electrically conductive liquid can carry electroporation energy from electrodes 530 to duodenal mucosa 122. In some embodiments, a hydrogel is used to electrically carry electroporation energy. In some cases the hydrogel may facilitate longer lasting contract of electroporation energy with duodenal mucosa 122, including within the crypts of duodenal mucosa 122.

Electrodes 530 can be analogous to electrodes 244 of electroporation device 200 as described above.

Referring to FIG. 6, another example electroporation device 600 embodiment is illustrated. Electroporation device 600 is an example of a weeping balloon design. That is, electroporation device 600 includes a balloon 610 that can be partly or fully made from a porous or microporous material such that an electrically conductive liquid or gel can elute, weep, or be otherwise transmitted through balloon 610 to form droplets 640. Electroporation device 600 is shown with balloon 610 in longitudinal cross-section to provide visibility within the interior space defined by balloon 610.

Electroporation device 600 includes balloon 610, a shaft 620, and one or more electrodes 630. Balloon 610 is circumferentially disposed about shaft 620. Electrodes 630 are disposed on the outer surface of shaft 620. Electrodes 630 can be analogous to electrodes 244 of electroporation device 200 as described above.

The size and materials of construction of balloon 610 can be analogous to those of balloon 510 described above.

Shaft 620 defines a lumen 622 that is analogous to lumen 212 of electroporation device 200. Shaft 620 also defines one or more apertures 626. Apertures 626 allow an electrically conductive liquid to flow from lumen 622 to an interior space of balloon 610 where electrically conductive liquid can be energized with electroporation energy from electrodes 630. Thereafter, the energized electrically conductive liquid can elute, weep, or be otherwise transmitted through balloon 610 to form droplets 640 that carrying electroporation energy to duodenal mucosa 122, including within the crypts of duodenal mucosa 122.

Figure 7:
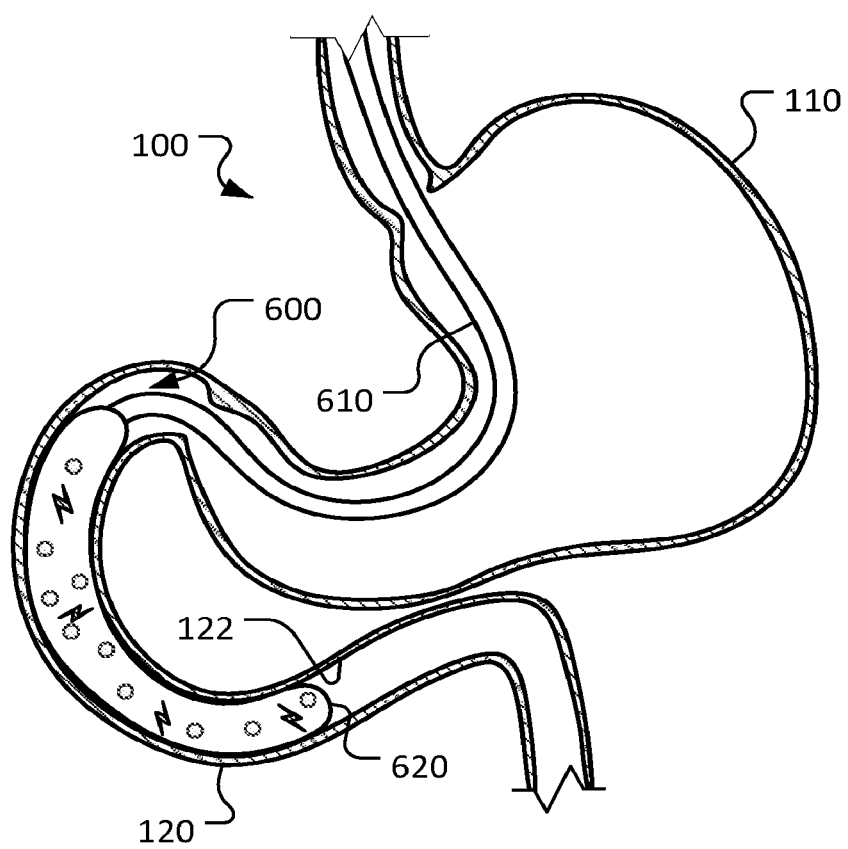
FIG. 7 shows the device of FIG. 5 or 6 deployed in a duodenum in an arrangement where the device can provide an electroporation treatment to modulate the duodenal mucosa.

Referring also to FIG. 7, electroporation device 600 can be deployed within duodenum 120 or more distally in the small intestines such as in the jejunum to provide electroporation treatments to a patient. Electroporation device 600 can treat obesity and diabetes using electroporation to modulate the duodenal or distal small intestinal mucosa 122. Electroporation device 500 (FIG. 5) can be implemented in an analogous manner.

Electroporation device 600 is shown after removal of a delivery device, such as endoscope 300 (FIG. 3) or a guiding wire. In some deployment techniques, endoscope 300 is used to position the balloon 620 in a desired location within duodenum 120. Then balloon 620 is inflated to temporarily fix balloon 620 in the desired location. Then, endoscope 300 can be further pulled back proximally (and may be completely disengaged from electroporation device 600.

With balloon 620 inflated, an electrically conductive liquid can be infused into the interior space of balloon 620 by injecting it via lumen 622 and apertures 626 (refer to FIG. 6). In some implementations, saline is used for electrically conductive liquid. In some implementations, hypertonic saline is used for electrically conductive liquid. In some implementations, dextrose is used for electrically conductive liquid. Other types of electrically conductive liquid can also be used. In some implementations, a combination of different types of electrically conductive liquid are used.

Electrodes 630 can be energized to provide a source of electroporation energy. The electrically conductive liquid within the interior space of balloon 610 will carry the electrical energy from the electrodes 630, through the wall of balloon 610, and to duodenal mucosa 122, including into the crypts of duodenal mucosa 122.

In some embodiments, a hydrogel is used to electrically carry electroporation energy. In some cases the hydrogel may facilitate longer lasting contract of electroporation energy with duodenal mucosa 122, including within the crypts of duodenal mucosa 122.

After administration of electroporation using electroporation device 600 and the electrically conductive liquid, the delivery of the electroporation energy can be stopped. Then balloon 620 can be deflated, and electroporation device 600 can be removed from GI tract 100 of the patient.

Figure 8:
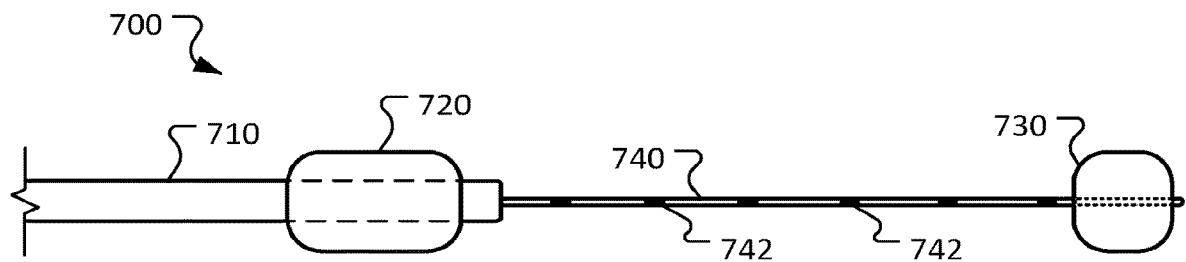
FIG. 8 is a plan view of another device for administering electroporation to a GI tract in accordance with some embodiments utilizing a proximal balloon mounted on an overtube on the endoscope. The electroporation catheter with its distal balloon is delivered through the working channel of the endoscope to deliver electroporation.
Figure 9:
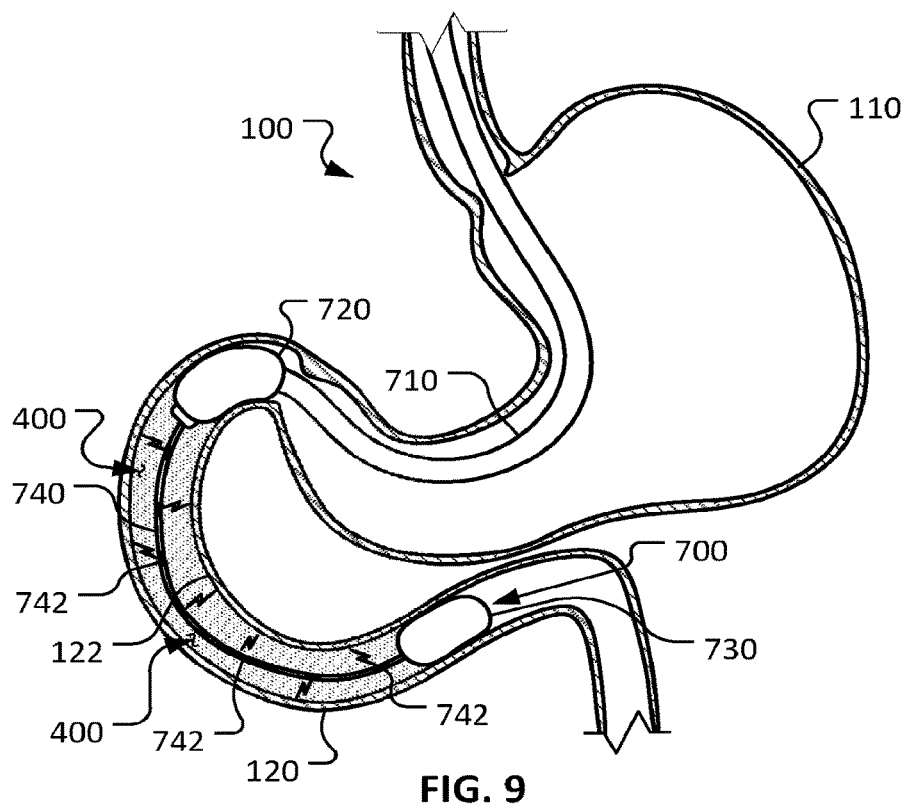
FIG. 9 shows the device of FIG. 8 deployed in a duodenum in an arrangement where the device can provide an electroporation treatment to modulate the duodenal mucosa.

Referring to FIGS. 8 and 9, another example electroporation device 700 embodiment is illustrated. Electroporation device 700 can be used to treat conditions such as obesity and diabetes using electroporation to modulate, for example, the duodenal mucosa 122.

In the depicted embodiment, electroporation device 700 includes an endoscope 710, a proximal balloon 720, a distal balloon 730, and a catheter 740 that includes one or more electrodes 742. Proximal balloon 720 is located at a distal end region of endoscope 710. Catheter 740 is configured to be slidably disposed within a working channel of endoscope 710. Distal balloon 730 is attached at a distal end region of catheter 740. Electrodes 742 are attached at spaced-apart locations along the length of catheter 740.

In some embodiments, proximal balloon 720 is attached to the distal end region of endoscope 710 (and endoscope 710 includes an inflation lumen). In some embodiments, proximal balloon 720 is attached to a distal portion of a sheath (not shown) that includes an inflation lumen, and that defines a larger lumen that can slidably receive endoscope 710.

Balloons 720 and 730 can be compliant balloons that are sized and constructed like balloons 220, 230 of electroporation device 200, for example. Electrodes 742 can be analogous to electrodes 244 of electroporation device 200 as described above.

Endoscope 710 includes a lumen (e.g., an irrigation lumen) through which electrically conductive liquid 400 can flow. When electroporation device 700 is in use (as depicted in FIG. 9), electrically conductive liquid 400 can flow through the lumen of endoscope 710, and thereafter reside in duodenum 120 between proximal balloon 720 and distal balloon 730. In this arrangement, energy from energized electrodes 742 can be conducted by electrically conductive liquid 400 to duodenal mucosa 122, including within the crypts of duodenal mucosa 122.

Figure 10:
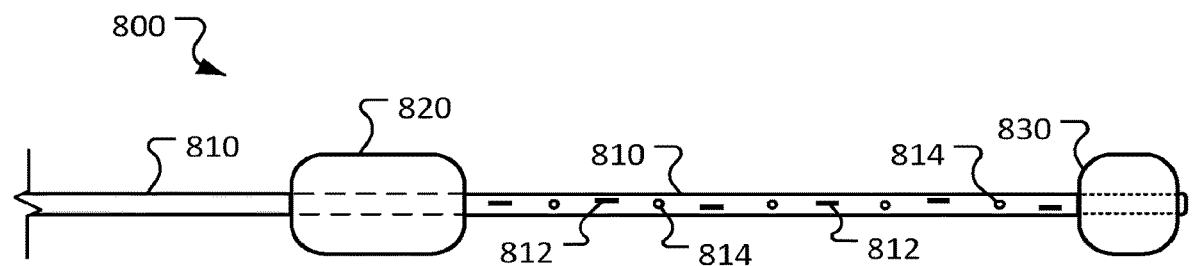
FIG. 10 is a plan view of another device for administering electroporation to a GI tract in accordance with some embodiments.
Figure 11:
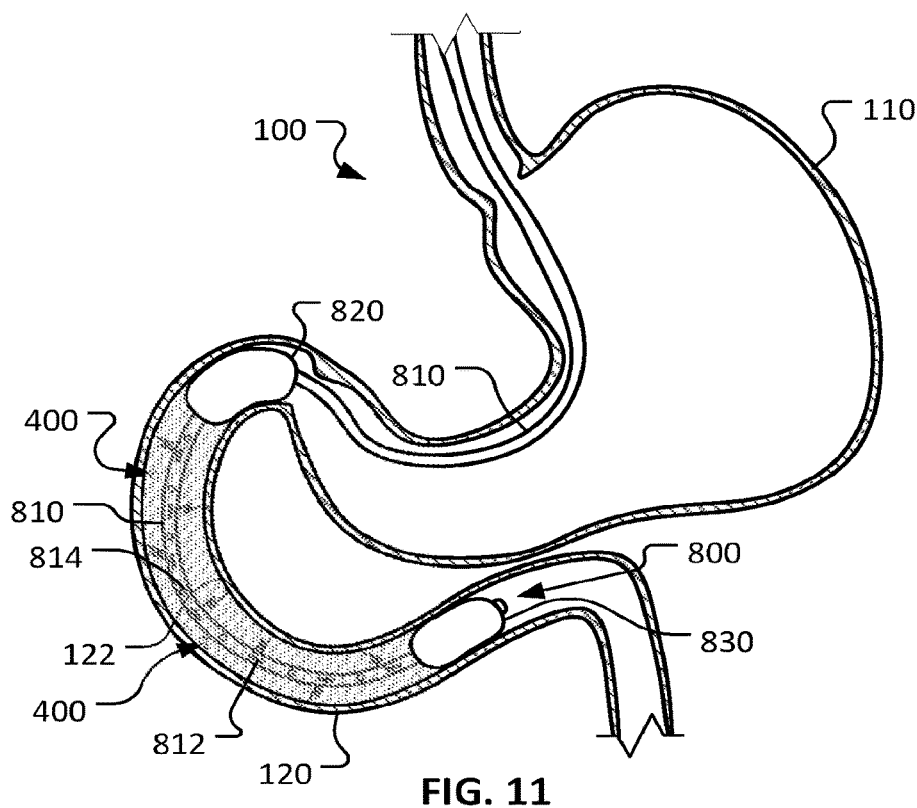
FIG. 11 shows the device of FIG. 10 deployed in a duodenum in an arrangement where the device can provide an electroporation treatment to modulate the duodenal mucosa.

Referring to FIGS. 10 and 11, another example electroporation device 800 embodiment is illustrated. Electroporation device 800 can be used to treat conditions such as obesity and diabetes using electroporation to modulate, for example, the duodenal mucosa 122. In some embodiments, electroporation device 800 is configured to be slidably disposed within a working channel of an endoscope such that electroporation device 800 can be delivered via the endoscope. In some embodiments, electroporation device 800 includes a lumen that can slidably receive a guidewire such that electroporation device 800 can be delivered over a wire.

In the depicted embodiment, electroporation device 800 includes catheter shaft 810, a proximal balloon 820, a distal balloon 830, one or more electrodes 812, and one or more apertures 814. Proximal balloon 820 is attached to catheter shaft 810 at any suitable distance proximal from the distal end of catheter shaft 810. Distal balloon 830 is attached at a distal end region of catheter shaft 810. Electrodes 842 are attached at spaced-apart locations along the length of catheter shaft 810. Apertures 814 are defined at spaced-apart locations along the length of catheter shaft 810.

Balloons 820 and 830 can be compliant balloons that are sized and constructed like balloons 220, 230 of electroporation device 200, for example. Electrodes 812 can be analogous to electrodes 244 of electroporation device 200 as described above.

Catheter shaft 810 defines one or more apertures 814 through which electrically conductive liquid 400 can flow. When electroporation device 800 is in use (as depicted in FIG. 11), electrically conductive liquid 400 can flow through a lumen of catheter shaft 810, exit catheter shaft 810 via apertures 814, and thereafter reside in duodenum 120 between proximal balloon 820 and distal balloon 830. In this arrangement, energy from energized electrodes 812 can be conducted by electrically conductive liquid 400 to duodenal mucosa 122, including within the crypts of duodenal mucosa 122.

Figure 12:
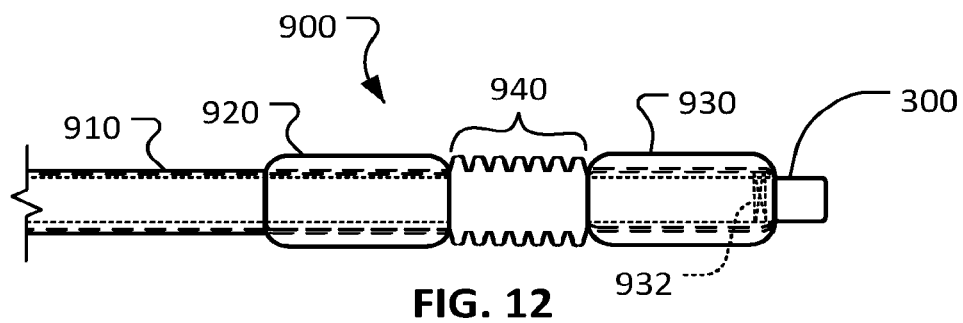
FIG. 12 is a plan view of another device for administering electroporation to a GI tract in accordance with some embodiments.
Figure 13:
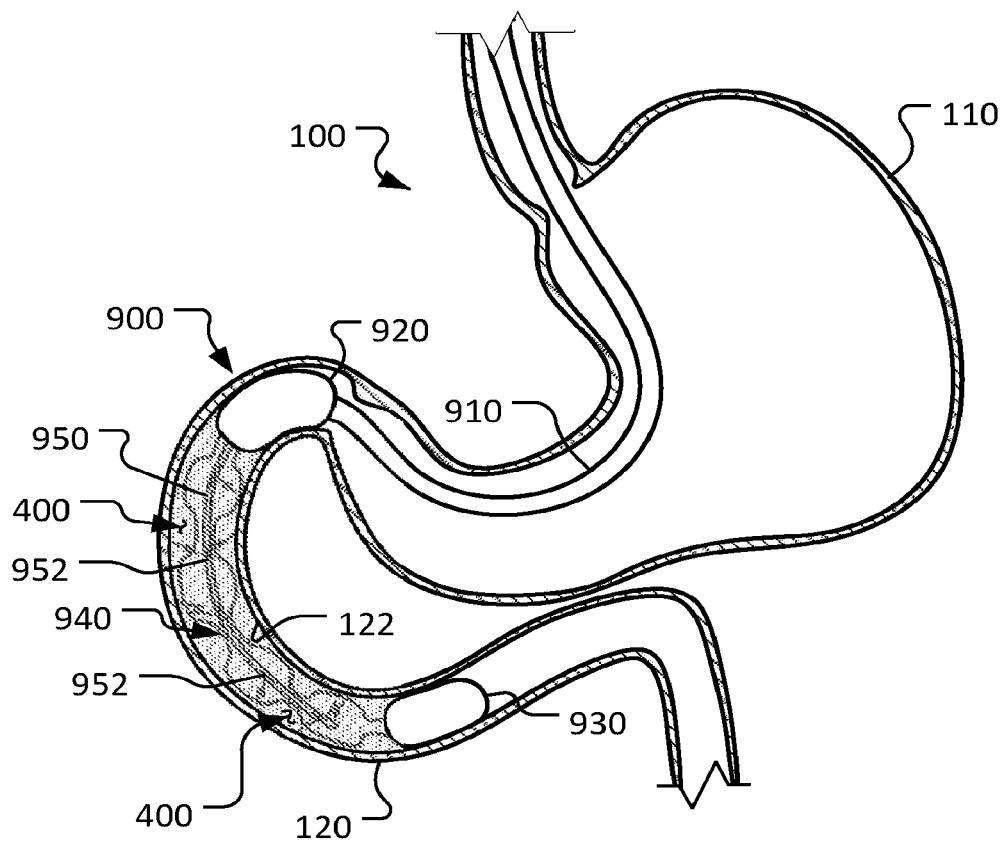
FIG. 13 shows the device of FIG. 12 deployed in a duodenum in an arrangement where the device can provide an electroporation treatment to modulate the duodenal mucosa.

Referring to FIGS. 12 and 13, another example electroporation device 900 embodiment is illustrated. Electroporation device 900 can be used to treat conditions such as obesity and diabetes using electroporation to modulate, for example, the duodenal mucosa 122.

In the depicted embodiment, electroporation device 900 includes an endoscope overtube 910, a proximal balloon 920, a distal balloon 930, a radially and/or longitudinally expandable middle portion 940, and an electroporation catheter 950 that includes one or more electrodes 952. An endoscope 300, along with the electroporation device 900, comprises an electroporation device system.

Proximal balloon 920 is attached to overtube 910 in a circumferential fashion. Middle portion 940 extends between proximal balloon 920 and distal balloon 930. Each of the overtube 910, proximal balloon 920, distal balloon 930, and middle portion 940 define a lumen that can slidably receive endoscope 300.

Within the lumen of distal balloon 930 is a distal valve 932. Valve 932 allows the passage of an instrument (e.g., endoscope 300 or guidewire) therethrough. But, when no such instrument is in contact with valve 932, valve 932 acts as a fluidic closure at the distal end of the lumen so that the lumen is dead ended at or near distal balloon 930.

Electroporation catheter 950 is configured to be slidably disposed within a working channel of endoscope 300 (as depicted in FIG. 13 where endoscope 300 has been pulled back such that its distal tip is within proximal balloon 920). Electrodes 952 are attached at spaced-apart locations along the length of electroporation catheter 950.

Balloons 920 and 930 can be compliant balloons that are sized and constructed like balloons 220, 230 of electroporation device 200, for example. Electrodes 952 can be analogous to electrodes 244 of electroporation device 200 as described above.

Middle portion 940 is made of a foldable mesh or porous material. Hence, middle portion 940 can be radially and/or longitudinally compressed (as shown in FIG. 12) for delivery of the electroporation device 900 into the GI tract. Additionally, middle portion 940 can be radially and/or longitudinally extended (as shown in FIG. 13) while electroporation device 900 is administering electroporation to modulate duodenal mucosa 122.

Endoscope 300 includes a lumen (e.g., an irrigation lumen) through which a supply of electrically conductive liquid 400 can be delivered as depicted in FIG. 13.

Using electroporation device 900 and endoscope 300 to deliver electroporation as depicted in FIG. 13, the depths and cell composition of the crypts and villi of duodenal mucosa 122 can be modulated. Using such devices and techniques, weight loss and/or control of diabetes by reducing the caloric absorption, by increasing gut hormones, and/or by re-setting the diseased intestinal mucosa of an individual can be achieved.

When electroporation device 900 is in use, electrically conductive liquid 400 can flow through the lumen of endoscope 300, pass through the porous material of middle portion 940, and thereafter reside in duodenum 120 between proximal balloon 920 and distal balloon 930. In this arrangement, energy from energized electrodes 952 can be conducted by electrically conductive liquid 400 to duodenal mucosa 122, including within the crypts of duodenal mucosa 122. In some cases, the irregular wall topography and/or crypts of duodenal mucosa 122 may become more planar by the mechanical forces applied by electroporation device 900 to duodenal mucosa 122.

ADDITIONAL EMBODIMENTS AND/OR ADDITIONAL FEATURES

In some embodiments, the electroporation devices and systems provided herein can include design features to prevent or inhibit undesired electro-stimulation of non-targeted bodily structures such as, but not limited to, the patient's heart and/or nervous system. For example, in some embodiments insulating elements can be included on or adjacent to one or more portions of the electroporation devices provided herein. Such insulating elements can block the emitted energy from following particular paths so as to protect non-targeted bodily structures. In some embodiments, insulated bipolar electroporation is incorporated (e.g., where the electrodes are mounted within or on a balloon, and/or separate electrodes are placed in the proximal duodenum). Such electrodes can be used as the anode or cathode when the complimentary cathode or anode are located within, on, or as a separate electrode to a balloon placed in the distal duodenum. For example, the insulation can be an insulating coating on a particular side of a balloon, a second balloon which insulated, or an air sac acting as insulation element to cover one side of the external surface of a balloon. In some embodiments, such insulating techniques can be used to cover one side of the external surface of a weeping balloon. In some embodiments, the energy delivery devices make use of the curvature of the duodenum to provide the desired electroporation without extra duodenum stimulation. In some embodiments, bipolar electrodes are included (e.g., a distal electrode and a proximal electrode on an electroporation device).

In some cases when the aforementioned insulation is included, because of the insulation on the external surface, the adjacent duodenal tissue to the insulated surface will require remaining treatment. To do this, for the proximal duodenum some embodiments use a return electrode in the greater curvature of the stomach, and for the distal and mid duodenum electrodes are placed in the proximal jejunum or other portions of the GI tract. These embodiments can be in alternatives or additions to the already described configuration with the return electrode placed on the abdomen, on the back, or somewhere else externally.

In some embodiments, undesired electro-stimulation of non-targeted bodily structures can be avoided or inhibited using a unique method of electroporation where pulse DC currents are delivered judicially at various times throughout the cardiac cycle. In some embodiments, continuous electroporation throughout the cardiac cycle is given; however, if ectopy or any change in the cardiac rhythm is noted, then that trigger (e.g., the far-field ventricular electrogram) can be used as the sensor wherein the energy delivery will be limited to only the first 200 msec, for example, following the detected far-field QRS. In some embodiments, an internal ECG sensor and electric field sensor can be placed on the insulated surface of the electroporation device. If there is no electric field pointing in the direction of heart, then substantially no danger of electroporation interfering with normal heart rhythm exists, and continuous electroporation can be carried out. If there is electric field pointing towards the direction of the heart, then the signal from the internal ECG sensor can be used for timing the electroporation pulse delivery so that the pulse is not delivered in the most vulnerable phase of heart rhythm.

While the implementations described above pertain to the delivery of electroporation to the duodenal cells relevant for the management of diabetes and obesity, the duodenum and the adjacent portions of the GI tract also offer unique vantage points to deliver electroporation and other energy delivery to neighboring structures. Such neighboring structures included, but are not limited to, the celiac ganglion and plexus, lymphatic ganglia and plexus, and the renal nerves and associated plexuses. Since the GI tract is curved and tortuous, bipolar electroporation can be carried out by deploying a distal electrode and a proximal electrodes along GI tract in such a way that the electric field created in between these two points will cover the visceral tissues and organs on the path outside of GI tract. Therefore, therapy can be delivered using some embodiments provided herein for the treatment of conditions such as, but not limited to, pancreatic malignancy, pancreatic and deep visceral pain and for hypertension by reversible and irreversible electroporation of the ganglia. Such hypertension management, in turn, would help with a metabolic syndrome that results from the combination of obesity, diabetes, and hypertension.

In some additional embodiments, stent devices for treating health conditions including obesity and diabetes are combination devices that combine the benefit of placing internal conduits covering the surface of the duodenal mucosa along with the benefits of more permanent electroporation-based modulation. By combining the two (a stent and electroporation electrodes), a system to secure the stent is attained. The conduit is essentially a covered stent, but instead of a crossing diamond-type of scaffold, linear struts are included. The purpose of the linear struts is to elute a gel which on electroporation will adhere to the mucosa, providing a secure hold. Between the linear struts, there is nothing apposing the covered stent to the duodenal mucosa so that secretions may still come out and enter the duodenal lumen. Food would pass through the stent, and thus a two-pronged approach for treating this region can be attained. Additional iterations could include one-way valves placed in between the linear struts, or a blood sugar sensor/RF feedback for electroporation release to titrate for an individual an ideal total energy load to maintain blood sugars.

In another embodiment using a stent conduit, the known benefits of a rouxen-Y procedure with that of electroporation are combined. Here, a deflectable catheter which has both an internal lumen for a wire, RF electrodes which can place energy on the central wire, and a second monorail wire is maneuvered out of the lumen of the proximal duodenum. The catheter is then moved to enter the proximal jejunum, and then is deflected back towards its initial entry site, and through the monorail lumen, a snare is used to grab the central lumen wire. Thus, a rail that essentially leaves the lumen and reenters, feeding back to itself is created. Over this wire, at least three iterations are possible: a) a covered stent/conduit is advanced over the distal wire, and then to secure it, a suture is advanced over both proximal and distal wires and tightened on the duodenum, b) the conduit is placed over the proximal wire following its course and essentially creating the anastomosis externally and with a similar locking mechanism to keep it in place, and c) there is a combination of the prior two such that a conduit, a covered stent, and a locking mechanism are all used in a given patient.

In some embodiments, the stent could be adjusted with noninvasive methods, including magnets or endoscopically placed stents, and the stent itself may be delivered via a laparoscopic approach.

Additionally, the devices and techniques described herein can be applied in contexts beyond that of the duodenum. For example, the devices and techniques described herein can be applied in the contexts of the mucosa of the distal small and large intestines, and other endoluminal organs such as the gallbladder, pancreas, and in the arteriovenous system.

Additionally, the devices and techniques describes herein can be applied to pherese drugs to cells within the mucosa of the duodenum 122 to alter their function. For example drugs such as rapamycin know to modulate the effects of paneth and stem cells within the crypts of the small intestines can be ionized and pheresed into these cell using electroporation. Furthermore, sweet substances known to stimulate the enteroendocrine cells within the villi of the duodenum can be applied. Similarly, tacrolimus can be used to stimulate stem cells in some cases. As such, these devices and techniques may cycle energy alone, drug or substance alone, or in combination to treat obesity and diabetes.

Some of the devices and methods provided herein can also incorporate stimulatory electrodes or other devices that can be used to ascertain cell death or activity, or to measure the temperature, electrical field strength, and/or charge density of the delivered electroporative therapy.

Some of the devices provided herein which incorporate a balloon or balloon-like elements may be used to achieve stretch of the intestine, not only to increase the surface area of contact to the crypt cells, but by virtue of the stretch itself produce membrane poration and induced apoptosis.

Some embodiments of the balloon or mesh incorporated devices are designed to increase the charge density of delivery through injection-like ports that may be achieved by a serrated surface or actual expandable, low surface area, pointed elements. These may serve as actual injection ports for charge or an electrolyte-rich solution to transfer the electroporation rendering energy or serve as regions of high electron or other electrical force density by virtue of their shape, which would match the required area where the increased density of charge is required and thus minimizing risks of electrical or thermal injury to the non-targeted sites.

It should be understood that one or more of the features described anywhere herein may be combined with one or more other features described anywhere herein to create hybrid devices and/or methods, without departing from the scope of this disclosure.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A method of treating diabetes in a patient, comprising:
    advancing an electroporation device comprising one or more electrodes into a duodenum of the patient; and
    delivering electroporation energy to mucosa of the duodenum using the one or more electrodes to treat diabetes, wherein the electroporation energy is delivered to crypts of the mucosa of the duodenum.

2. The method of claim 1 further comprising transitioning the electroporation device from a first configuration to a second configuration.

3. The method of claim 2, wherein the first configuration is a contracted configuration and the second configuration is an expanded configuration.

4. The method of claim 2, wherein transitioning the electroporation device to the second configuration stretches at least a portion of the duodenum.

5. The method of claim 1, wherein the electroporation energy comprises pulse currents.

6. The method of claim 1, wherein the one or more electrodes comprise bipolar electrodes.

7. The method of claim 1, wherein the one or more electrodes comprise a plurality of spaced-apart electrodes.

8. The method of claim 1, wherein the electroporation device comprises a rolled-up member comprising the one or more electrodes.

9. The method of claim 8, wherein the one or more electrodes are disposed on an outer surface of the rolled-up member.

10. The method of claim 8, wherein the rolled-up member defines one or more apertures.

11. The method of claim 8 further comprising delivering a fluid into an interior space of the duodenum through the one or more apertures.

12. The method of claim 11, wherein the fluid is circulated in the interior space of the duodenum while delivering the electroporation energy.

13. The method of claim 11, wherein at least a portion of the rolled-up member is spaced apart from an inner wall of the duodenum, and wherein the fluid conducts at least some of the electroporation energy to the inner wall of the duodenum.

14. The method of claim 11, wherein the fluid comprises a hydrogel.

15. The method of claim 11, wherein the fluid comprises an electrically conductive liquid.

16. The method of claim 11, wherein the fluid comprises a drug.

17. The method of claim 16, wherein delivering the fluid comprises pheresing the drug to cells within the mucosa of the duodenum.

18. The method of claim 8, wherein the rolled-up member defines a lumen and the method further comprises advancing an endoscope through the lumen of the rolled-up member.

19. The method of claim 1 further comprising measuring one or more characteristics of the delivered electroporation energy.

20. The method of claim 1, wherein the electroporation energy treats the entirety of a circumferential portion of the duodenum.

21. The method of claim 1, wherein delivering electroporation energy comprises delivering irreversible electroporation energy.

22. The method of claim 1, wherein the electroporation energy resets diseased mucosa of the duodenum.

23. The method of claim 1, wherein the electroporation energy increases a level of a gut hormone important in appetite regulation.

24. The method of claim 1, wherein the electroporation energy increases a level of a gut hormone important in insulin secretion.

25. The method of claim 1, wherein the electroporation energy reshapes the mucosa of the duodenum.

* * * * *